United States Patent
Kim et al.

(10) Patent No.: US 9,777,031 B2
(45) Date of Patent: *Oct. 3, 2017

(54) COMPLEX AND PREPARATION METHOD OF POLY(ALKYLENE CARBONATE) USING THE SAME

(71) Applicants: SK Innovation Co., Ltd., Seoul (KR); SK Global Chemical Co., Ltd., Seoul (KR)

(72) Inventors: Jong Chan Kim, Daejeon (KR); Han Sol Lee, Daejeon (KR); Hyo Seung Park, Daejeon (KR); Je Ho Lee, Daejeon (KR); Jeong Hyun Noh, Daejeon (KR); Jong Ho Lim, Daejeon (KR); Jeon Koo Lee, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 34 days.

This patent is subject to a terminal disclaimer.

(21) Appl. No.: 14/903,453

(22) PCT Filed: Jul. 4, 2014

(86) PCT No.: PCT/KR2014/005998
§ 371 (c)(1),
(2) Date: Jan. 7, 2016

(87) PCT Pub. No.: WO2015/005616
PCT Pub. Date: Jan. 15, 2015

(65) Prior Publication Data
US 2016/0376299 A1  Dec. 29, 2016

(30) Foreign Application Priority Data

Jul. 9, 2013 (KR) .................. 10-2013-0080526
Jun. 24, 2014 (KR) .................. 10-2014-0077064

(51) Int. Cl.
*C08G 59/00* (2006.01)
*C07F 15/06* (2006.01)
*C08G 64/34* (2006.01)

(52) U.S. Cl.
CPC ............ *C07F 15/065* (2013.01); *C08G 64/34* (2013.01)

(58) Field of Classification Search
CPC ..... C07F 15/065; C07F 11/005; C08G 65/266
See application file for complete search history.

(56) References Cited

U.S. PATENT DOCUMENTS

| | | |
|---|---|---|
| 4,528,364 A | 7/1985 | Prier |
| 4,686,276 A | 8/1987 | Myers |
| 4,826,887 A | 5/1989 | Kuyper et al. |
| 4,931,486 A | 6/1990 | Myers |
| 5,066,762 A | 11/1991 | Ohbuchi et al. |
| 5,070,173 A | 12/1991 | Yokota et al. |
| 5,171,830 A | 12/1992 | Grey |
| 5,847,069 A | 12/1998 | Greco |
| 5,863,627 A | 1/1999 | Szycher et al. |
| 6,197,051 B1 | 3/2001 | Zhong |
| 8,247,520 B2 | 8/2012 | Allen et al. |
| 8,530,616 B2 | 9/2013 | Jeong et al. |
| 8,598,309 B2 | 12/2013 | Jeong et al. |
| 8,987,411 B2 | 3/2015 | Jeong et al. |
| 9,115,161 B2 | 8/2015 | Lee et al. |
| 9,327,280 B2 | 5/2016 | Lee et al. |
| 2010/0121026 A1 | 5/2010 | Lee et al. |
| 2011/0230580 A1 | 9/2011 | Allen et al. |
| 2011/0245424 A1 | 10/2011 | Jeong et al. |
| 2015/0051369 A1* | 2/2015 | Allen ................ C08G 64/34 528/405 |
| 2016/0304664 A1 | 10/2016 | Kim et al. |

FOREIGN PATENT DOCUMENTS

| | | |
|---|---|---|
| CN | 1060299 A | 4/1992 |
| CN | 101020747 A | 8/2007 |
| CN | 101327452 A | 12/2008 |
| CN | 101687987 A | 3/2010 |
| CN | 102212085 A | 10/2011 |
| CN | 102939319 A | 2/2013 |
| EP | 0222453 A2 | 5/1987 |
| EP | 0302712 A2 | 2/1989 |
| EP | 0311278 A1 | 4/1989 |
| EP | 0798328 A2 | 10/1997 |
| KR | 100853358 B1 | 8/2008 |
| KR | 1020090090154 A | 8/2009 |
| KR | 1020100067593 A | 6/2010 |
| KR | 1020100136310 A | 12/2010 |
| KR | 1020110097282 A | 8/2011 |

(Continued)

OTHER PUBLICATIONS

Biannic et al., "Efficient Cobalt-Catalyzed Oxidative Conversion of Lignin Models to Benzoquinones", Organic Letters, May 16, 2013, p. 2730-2733 vol. 15, No. 11.

Cao et al., "Crosslinked polycarbonate polyurethanes: preparation and physical properties", Polymer, 1992, p. 1384-1390, vol. 33, No. 7.

Gunatillake et al., "Synthesis and Characterization of a Series of Poly(alkylene carbonate) Macrodiols and the Effect of Their Structure on the Properties of Polyurethanes", Journal of Applied Polymer Science, 1998, p. 1621-1633, vol. 69.

(Continued)

*Primary Examiner* — Shane Fang
(74) *Attorney, Agent, or Firm* — The Webb Law Firm

(57) ABSTRACT

The present invention is directed to a novel complex synthesized from a Salen-type ligand. The novel complex contains a quaternary ammonium salt. The present invention is also directed to a preparation method of a copolymer of carbon dioxide and epoxide using the complex synthesized from a Salen-type ligand as a catalyst.

17 Claims, No Drawings

(56) References Cited

FOREIGN PATENT DOCUMENTS

| KR | 1020110112061 A | 10/2011 |
| WO | 9857671 A2 | 12/1998 |
| WO | 2008136591 A1 | 11/2008 |
| WO | 2012158573 A1 | 11/2012 |
| WO | 2013090276 A1 | 6/2013 |
| WO | 2014148825 A1 | 9/2014 |

OTHER PUBLICATIONS

Harris et al., "Polyurethane Elastomers Based on Molecular Weight Advanced Poly(ethylene Ether Carbonate) Diols. I. Comparison to Commercial Diols", Journal of Applied Polymer Science, 1990, p. 487-507, vol. 41.

Harris et al., "Structural Features of Poly(Alkylene Ether Carbonate) Diols and Intermediates Formed during Their Preparation", Journal of Applied Polymer Science, 1989, p. 1491-1511, vol. 37.

Kuran, "Poly(Propylene Carbonate)", Polymeric Materials Encyclopedia, 1996, p. 6623, vol. 9.

Lu et al., "Cobalt catalysts for the coupling of CO2 and epoxides to provide polycarbonates and cyclic carbonates", Chem. Soc. Rev., 2012, p. 1462-1484, vol. 41.

Min et al., "Efficient Synthesis of a Highly Active Catalyst for CO2/Epoxide Copolymerization", Bull. Korean Chem. Soc., 2009, p. 745-748, vol. 30, No. 3.

Na et al., "Elucidation of the Structure of a Highly Active Catalytic System for CO2/Epoxide Copolymerization: a salen-Cobaltate Complex of an Unusual Binding Mode", Inorganic Chemistry, Sep. 25, 2009, p. 10455-10465, vol. 48.

Noh et al., "Two Components in a Molecule: Highly Efficient and Thermally Robust Catalytic System for CO2/Epoxide Copolymerization", Journal of American Chemical Society, Jun. 8, 2007, p. 8082-8083, vol. 129.

S et al., "A Highly Active and Recyclable Catalytic System for CO2/Propylene Oxide Copolymerization", Angew. Chem. Int. Ed., 2008, p. 7306-7309, vol. 47.

\* cited by examiner

COMPLEX AND PREPARATION METHOD OF POLY(ALKYLENE CARBONATE) USING THE SAME

CROSS-REFERENCE TO RELATED APPLICATIONS

This application is the United States national phase of International Application No. PCT/KR2014/005998 filed Jul. 4, 2014, and claims priority to Korean Patent Application Nos. 10-2013-0080526 and 10-2014-0077064, filed Jul. 9, 2013 and Jun. 24, 2014, respectively, the disclosures of which are hereby incorporated in their entirety by reference.

TECHNICAL FIELD

The following disclosure relates to a novel complex and a preparation method of poly(alkylene carbonate) using the same, and more specifically, to a novel complex synthesized from a Salen-type ligand containing a quaternary ammonium salt and a preparation method of poly(alkylene carbonate) using the same as a catalyst.

BACKGROUND ART

Poly (alkylene carbonate) is an easily biodegradable polymer and is useful for packaging or coating materials. Methods of preparing poly(alkylene carbonate) from an epoxide compound and carbon dioxide are highly eco-friendly in that phosgene which is harmful compound is not used and carbon dioxide is obtained at a low cost.

Since 1960's, many researchers have developed various types of catalysts to prepare poly(alkylene carbonate) from an epoxide compound and carbon dioxide. Recently, a catalyst having high activity and high selectivity and synthesized from a Salen: ([H$_2$ Salen=N,N'-bis(3,5-dialkylsalicylidene)-1,2-ethylenediamine]-type ligand containing a quaternary ammonium salt has been published [Korean Patent Registration No. 10-0853358 (Registration Date: Aug. 13, 2008); Korean Patent Application No. 10-2008-0015454 (Filing Date: Feb. 20, 2008); PCT/KR2008/002453 (Filing Date: Apr. 30, 2008); J. Am. Chem. Soc. 2007, 129, 8082-8083 (Jul. 4, 2007); Angew. Chem. Int. Ed., 2008, 47, 7306-7309 (Sep. 8, 2008)]. The catalyst disclosed in Korean Patent Registration No. 10-0853358 shows high activity and high selectivity, and may provide a copolymer having a large molecular weight and may be polymerized at a high temperature to be applicable to commercial processes. Furthermore, this catalyst is advantageous because a quaternary ammonium salt is contained in the ligand, and thus the catalyst may be easily separated from a copolymer resulting from copolymerization of carbon dioxide and epoxide, and re-used.

Also, the inventors of Korean Patent Registration No. 10-0853358 have carefully examined a structure of a particular catalyst having higher activity and higher selectivity as compared to other group among the catalyst group disclosed in the above patent, and have proved that such a catalyst has a peculiar structure in which nitrogen of the Salen ligand is not coordinated to a metal but oxygen thereof only is coordinated thereto, which was not known until now (see Structure 1 below, Inorg. Chem. 2009, 48, 10455 10465).

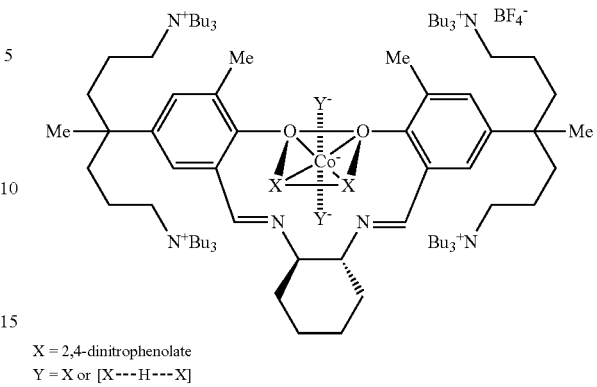

X = 2,4-dinitrophenolate
Y = X or [X---H---X]

Furthermore, a method of easily synthesizing the ligand of the compound of Structure 1 has been developed (Bull. Korean Chem. Soc. 2009, 30, 745-748).

Poly(alkylene carbonate) having a high molecular weight may be economically prepared using the compound of Structure 1 as a highly active catalyst. However, since poly(alkylene carbonate) has a low glass transition temperature (which is 40° C. in the case of poly(alkylene carbonate) prepared from propylene oxide and carbon dioxide) and has insufficient mechanical strength, predetermined limitations are imposed on the applications that may be developed therewith.

With the way of overcoming the limitations of poly (alkylene carbonate), methods of preparing poly(alkylene carbonate)polyol having a low molecular weight and a plurality of —OH terminal groups and preparing polyurethane therefrom have been developed. Polyurethane is a polymer obtained by reacting a compound having an —OH group with a compound having an isocyanate (—NCO) group thus forming a urethane bond (—NHC(O)O—). A variety of compounds having an —NCO group have been used, a variety of compounds having an —OH group have been developed, and thermoplastic or thermosetting plastics or elastomeric polyurethanes having various physical properties have been developed and used. Examples of the compound having an —OH group mainly represent diols and polyester diols having —OH terminal groups at end groups, which have thousands of molecular weights obtained by ring-opening polymerization of ethylene oxide or propylene oxide. Attempts have been made to prepare poly(alkylene carbonate)diol or polyol to thereby attain polyurethane rather than poly(alkylene oxide)diol or polyester diol (W. Kuran, Polymeric Materials Encyclopedia, J. C. Salamone, Ed. CRC Press, Inc., Boca Raton 1996, Vol. 9, p. 6623; Polymer, 1992, vol 33, 1384-1390). Polyurethane prepared from poly(alkylene carbonate)polyol is known to have higher hydrolyzability compared to polyurethane prepared from polyester polyol (European Patent No. 302712; U.S. Pat. No. 5,863,627), and is also reported to have greater antistatic effects (U.S. Pat. No. 4,931,486). Furthermore, thrombus coagulation resistance is reported to be high (PCT International Patent Laid-Open Publication No. 9857671).

European Patent No. 302712 (priority date: Aug. 4, 1987) and European Patent No. 311278 (priority date: Oct. 6, 1987) disclose polycarbonate diol prepared by condensing diethylcarbonate (EtOC(O)OEt) and 1,6-hexanediol or 1,5-petandediol, and preparation of polyurethane using the same. In addition, U.S. Pat. No. 5,171,830 (filing date: Aug.

16, 1991) discloses a method of synthesizing poly(alkylene carbonate) by condensing dialkyl carbonate (ROC(O)OR) and alpha, omega-alkanediol having 4 or more carbons in the presence of a base catalyst and preparation of a urethane resin using the same.

European Patent No. 798328A2 (priority date: Mar. 28, 1996) discloses synthesis of polycarbonate-co-polyether diol using condensation of polyether diol and dimethylcarboante (MeOC(O)OMe).

Also, synthesis of poly(alkylene carbonate)macrodiol by condensation of various diol compounds and ethylene carbonate and preparation of polyurethane using the same are disclosed in *J. Appl. Polym. Sci.* 1998, 69, 1621-1633 and *J. Appl. Polym. Sci.* 1989, 37, 1491-1511.

However, such poly(alkylene carbonate)polyol is not prepared using copolymerization of carbon dioxide and epoxide and also has a different structure from that of a copolymer of carbon dioxide and epoxide. Specifically, in order to prepare poly(alkylene carbonate) using condensation of ethylene carbonate or dialkyl carbonate, diol having spaced 3 or more carbons should be used. That is, poly(alkylene carbonate) has a structure in which a carbonate bond is linked by 3 or more carbons. Poly(alkylene carbonate) prepared by copolymerization of carbon dioxide and epoxide has a structure in which a carbonate bond is linked by 2 carbons.

U.S. Pat. No. 4,686,276 (filing date: Dec. 30, 1985) discloses a method of synthesizing poly(ethylene carbonate) diol by copolymerizing carbon dioxide and ethylene oxide in the presence or absence of ethylene carbonate using a diol compound as an initiator and a catalyst consisting of an alkaline compound and a tin compound. In addition, U.S. Pat. No. 4,528,364 (filing date: Apr. 19, 1984) discloses a method of removing a catalyst from the prepared polymer compound. Here, the prepared polymer has a carbon dioxide content less than 30%, which is not a complete alternating copolymer. In addition, preparation of polyurethane using poly(ethylene carbonate)diol which was prepared and purified by the above method is disclosed in *Journal of Applied Polymer Science*. 1990, 41, 487 507.

European Patent No. 0222453 (filing date: Jun. 11, 1986) discloses a method of synthesizing polyol by copolymerizing carbon dioxide and epoxide using a double metal cyanide compound as a catalyst and using an organic material having reactive hydrogen as a molecular weight regulator. However, the obtained polyol has a carbon dioxide content of 5 to 13 mol %, which is not a pure poly(alkylene carbonate) compound based on complete alternating copolymerization of carbon dioxide and epoxide.

CN Patent No. 1060299A (filing date: Sep. 19, 1991), which was published later, discloses a preparation method of polyol by copolymerizing carbon dioxide and epoxide using a polymer-supported bimetallic catalyst and using an organic material having 1 to 10 reactive hydrogen as a molecular weight regulator. However, the polyol prepared by Examples has a carbon dioxide content of 37 to 40 mol %, which is not a pure poly(alkylene carbonate) compound based on complete alternating copolymerization of carbon dioxide and epoxide.

U.S. Pat. No. 8,247,520 (filing date: Sep. 8, 2009) discloses a method of copolymerizing carbon dioxide and epoxide using a chain transfer agent which is a molecular weight regulator under a binary catalyst system of (Salen)Co compound. However, the present inventors found that as an amount of the used chain transfer agent becomes increased in the copolymerization system, catalyst system activity is deteriorated, such that there is a limitation in obtaining a low molecular weight of copolymer having desirable level.

As described above, synthesis of a low molecular weight of poly(alkylene carbonate) by copolymerization of carbon dioxide and epoxide in the presence of a molecular weight regulator has been abundantly reported. Meanwhile, in order to prepare appropriate poly(alkylene carbonate) having a molecular weight required in a large-scale commercial process, since maintenance of catalyst system activity in the preparation process as well as economical cost of copolymerization catalyst system are important, development of a novel catalyst system capable of satisfying the requirements has been demanded.

DISCLOSURE OF INVENTION

Technical Problem

An embodiment of the present invention is directed to providing a novel complex of which a catalytic activity is effectively maintained in a process of preparing poly(alkylene carbonate).

Another embodiment of the present invention is directed to providing a preparation method of poly(alkylene carbonate) using a molecular weight regulator in the presence of the novel complex as a catalyst.

Solution to Problem

In one general aspect, the present invention provides a novel complex capable of being signficantly and effectively used in preparing poly(alkylene carbonate), the novel complex represented by the following Chemical Formula 1:

[Chemical Formula 1]

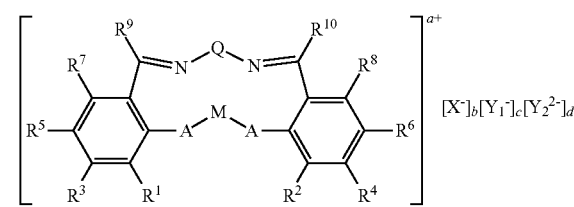

in Chemical Formula 1,
M is trivalent cobalt or trivalent chromium;
A is oxygen or sulfur;
Q is a diradical connecting two nitrogens;
$R^1$ to $R^{10}$ are each independently hydrogen; halogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20) alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20) alkyl; (C6-C20)aryl(C1-C20)alkyl containing one or more selected from among halogen, nitrogen, oxygen, silicon, sulfur and phosphorus; (C1-C20)alkoxy; (C6-C30)aryloxy; formyl; (C1-C20)alkylcarbonyl; (C6-C20)arylcarbonyl; a metalloid radical of Group 14 metal substituted with hydrocarbyl; a protonated group of the following Chemical Formula 2; a protonated group of the following Chemical Formula 3; a protonated group of the following Chemical Formula 4; a protonated group of the following Chemical Formula 5; a protonated group of the following Chemical Formula 6; a protonated group of the following Chemical Formula 7; a protonated group of the following Chemical Formula 8; or a protonated group of the following Chemical Formula 9;

wherein at least one or more of $R^1$ to $R^{10}$ are a protonated group selected from a group consisting of the following Chemical Formulas 2, 3, 4, 5, 6, 7, 8, and 9;

[Chemical Formula 2]

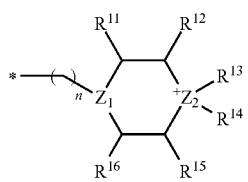

[Chemical Formula 3]

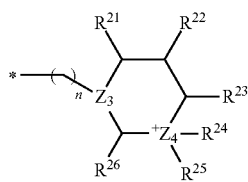

[Chemical Formula 4]

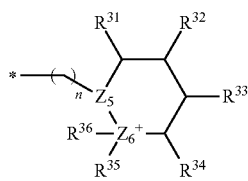

[Chemical Formula 5]

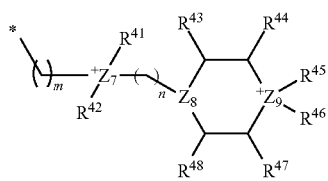

[Chemical Formula 6]

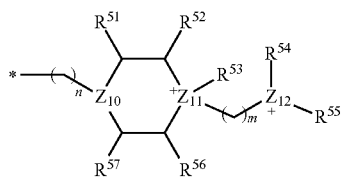

[Chemical Formula 7]

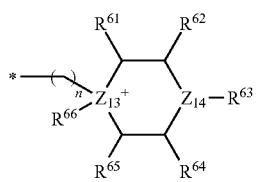

[Chemical Formula 8]

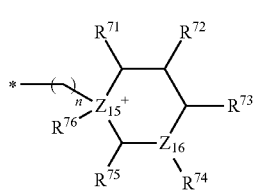

[Chemical Formula 9]

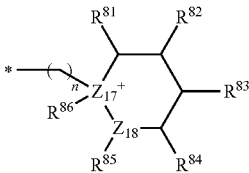

$X^-$ is halogen anion; a (C6-C20)aryloxy anion; a (C6-C20)aryloxy anion containing one or more selected from among halogen, nitrogen, oxygen, silicon, sulfur and phosphorus; a (C1-C20)alkylcarboxy anion; a (C1-C20)alkylcarboxy anion containing one or more selected from among halogen, nitrogen, oxygen, silicon, sulfur and phosphorus; a (C6-C20)arylcarboxy anion; a (C6-C20)arylcarboxy anion containing one or more selected from among halogen, nitrogen, oxygen, silicon, sulfur and phosphorus; a (C1-C20)alkoxy anion; a (C1-C20)alkoxy anion containing one or more selected from among halogen, nitrogen, oxygen, silicon, sulfur and phosphorus; a (C1-C20)alkylcarbonate anion; a (C1-C20)alkylcarbonate anion containing one or more selected from among halogen, nitrogen, oxygen, silicon, sulfur and phosphorus; a (C6-C20)arylcarbonate anion; a (C6-C20)arylcarbonate anion containing one or more selected from among halogen, nitrogen, oxygen, silicon, sulfur and phosphorus; a (C1-C20)alkylsulfonate anion; a (C1-C20)alkylsulfonate anion containing one or more selected from among halogen, nitrogen, oxygen, silicon, sulfur and phosphorus; a (C1-C20)alkylamido anion; a (C1-C20)alkylamido anion containing one or more selected from among halogen, nitrogen, oxygen, silicon, sulfur and phosphorus; a (C6-C20)arylamido anion; a (C6-C20)arylamido anion containing one or more selected from among halogen, nitrogen, oxygen, silicon, sulfur and phosphorus; a (C1-C20)alkylcarbamate anion; a (C1-C20)alkylcarbamate anion containing one or more selected from among halogen, nitrogen, oxygen, silicon, sulfur and phosphorus; a (C6-C20)arylcarbamate anion; or a (C6-C20)arylcarbamate anion containing one or more selected from among halogen, nitrogen, oxygen, silicon, sulfur and phosphorus;

$X^-$ may be coordinated to M;

$Y_1^-$ is $F^-$, $Cl^-$, $Br^-$, $I^-$, $BF_4^-$, $ClO_4^-$, $NO_3^-$ or $PF_6^-$;

$Y_2^{2-}$ is $SO_4^{2-}$ or $CO_3^{2-}$;

a is an integer obtained by adding 1 to the total number of monovalent cations included in protonated groups of $R^1$ to $R^{10}$;

b is an integer of 1 or more, c is an integer of 0 or more, d is an integer of 0 or more, and b+c+2d=a is satisfied;

$Z_1$ to $Z_{18}$ are each independently a nitrogen or phosphorus atomus;

n is an integer of 1 to 10;

m is an integer of 1 to 10;

$R^{11}$ to $R^{16}$, $R^{21}$ to $R^{26}$, $R^{31}$ to $R^{36}$, $R^{41}$ to $R^{48}$, $R^{51}$ to $R^{57}$, $R^{61}$ to $R^{66}$, $R^{71}$ to $R^{76}$ and $R^{81}$ to $R^{86}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{11}$ to $R^{16}$, two of $R^{21}$ to $R^{26}$, two of $R^{31}$ to $R^{36}$, two of $R^{43}$ to $R^{48}$, two of $R^{51}$ to $R^{57}$, two of $R^{61}$ to $R^{66}$, two of $R^{71}$ to $R^{76}$, and two of $R^{81}$ to $R^{86}$ may be linked with each other to thereby form a ring; and wherein alkyl, alkenyl, alkylaryl, arylalkyl, alkoxy, aryloxy, alkylcarbonyl, and arylcarbonyl of $R^1$ to $R^{10}$, and alkyl, alkenyl, alkylaryl and arylalkyl of $R^{11}$ to $R^{16}$, $R^{21}$ to $R^{26}$, $R^{31}$ to $R^{36}$, $R^{41}$ to $R^{48}$, $R^{51}$ to $R^{57}$, $R^{61}$ to $R^{66}$, $R^{71}$ to $R^{76}$ and $R^{81}$ to $R^{86}$ may be further substituted with any one or more selected from halogen, (C1-C20)alkyl, (C2-C20)alkenyl, (C1-C20)alkyl(C6-C20)aryl and (C6-C20)aryl(C1-C20)alkyl.

The novel complex represented by Chemical Formula 1 above includes one or more protonated groups represented by Chemical Formulas 2 to 9 above to have significantly excellent activity and high activity even at a low temperature, thereby being significantly effective in preparation of poly(alkylene carbonate).

That is, since the complex represented by Chemical Formula 1 above of the present invention structurally includes at least one or more onium salts in a molecule, the complex used as a catalyst may have excellent activity and promote polymerization even at a relatively low temperature.

In addition, the complex represented by Chemical Formula 1 of the present invention includes at least one protonated group having an amine functional group and an onium salt or phosphine or an onium salt in a molecule, such that activity may be excellent and high activity may be maintained even at a low temperature.

The complex represented by Chemical Formula 1 of the present invention includes a structure in which an amine functional group and an onium salt or phosphine and an onium salt are symmetrically present at both sides based on a central metal, respectively, and preferably, when the structure of the complex is symmetrically present, the preparation yield of the complex may be improved, and activity may be excellent at the time of preparation of poly(alkylene carbonate).

Q may be (C6-C30)arylene, (C1-C20)alkylene, (C2-C20)alkenylene, (C2-C20)alkynylene or (C3-C20)cycloalkylene, and more specifically, M may be trivalent cobalt; A may be oxygen; and Q may be 1,2-cyclohexylene, phenylene or ethylene.

At least one or more of $R^1$, $R^2$, $R^5$ and $R^6$ may be a protonated group selected from a group consisting of Chemical Formulas 2, 3, 4, 5, 6, 7, 8, and 9 as described above, and more specifically, $R^3$, $R^4$, $R^7$, $R^8$, $R^9$ and $R^{10}$ may be hydrogen.

In order to have excellent catalytic activity, Chemical Formula 1 above may be represented by the following Chemical Formula 11:

in Chemical Formula 11,

M is trivalent cobalt or trivalent chromium;

A is oxygen or sulfur;

$R^1$ and $R^2$ are each independently a protonated group selected from a group consisting of hydrogen, (C1-C10) alkyl, Chemical Formulas 2, 3, 4, 5, 6, 7, 8, and 9 as described above;

$R^5$ and $R^6$ each independently represent hydrogen, halogen, (C1-C20)alkyl, (C2-C20)alkenyl, (C1-C20)alkoxy, (C1-C20)alkyl(C6-C20)aryl or (C6-C20)aryl(C1-C20)alkyl; alkyl, alkenyl, alkoxy, alkylaryl or arylalkyl of $R^5$ or $R^6$ may be further substituted with any one or more selected from halogen, (C1-C20)alkyl, (C2-C20)alkenyl, (C1-C20)alkoxy, (C1-C20)alkyl(C6-C20) aryl or (C6-C20)aryl(C1-C20) alkyl;

$X_1^-$ is halogen anion; a (C1-C20)alkylcarboxy anion; a (C1-C20)alkylcarboxy anion containing one or more selected from among halogen, nitrogen, oxygen, silicon, sulfur and phosphorus; a (C1-C20)alkylcarbonate anion; a (C1-C20)alkylcarbonate anion containing one or more selected from among halogen, nitrogen, oxygen, silicon, sulfur and phosphorus; a (C1-C20)alkylcarbamate anion; or a (C1-C20)alkylcarbamate anion containing one or more selected from among halogen, nitrogen, oxygen, silicon, sulfur and phosphorus; a (C6-C20)aryloxy anion; or a (C6-C20)aryloxy anion containing one or more selected from among halogen, nitrogen, oxygen, silicon, sulfur and phosphorus;

$X_1^-$ may be coordinated to Co;

$Y_1^-$ is $Cl^-$, $Br^-$, $BF_4^-$ or $NO_3^-$;

$Y_2^{2-}$ is $SO_4^{2-}$ or $CO_3^{2-}$;

a is an integer obtained by adding 1 to the total number of monovalent cations included in protonated groups of $R^1$ to $R^2$; and b is an integer of 1 or more, c is an integer of 0 or more, d is an integer of 0 or more, and b+c+2d=a is satisfied.

In order to have a more excellent catalytic activity, preferably, the complex represented by Chemical Formula 1 above may have a structure represented by any one of the following Chemical Formulas 12 to 22.

That is, in the complex having one structure represented by the following Chemical Formulas 12 to 22, one or two onium salt(s) are symmetrically or asymmetrically present at based on a central metal, respectively, more specifically, a structure having amine and an onium salt or phosphine and an onium salt is asymmetrically present at one side or symmetrically present at both sides, based on a central metal, such that the complex used as a catalyst in preparation of poly(alkylene carbonate) may have excellent catalytic activity.

[Chemical Formula 11]

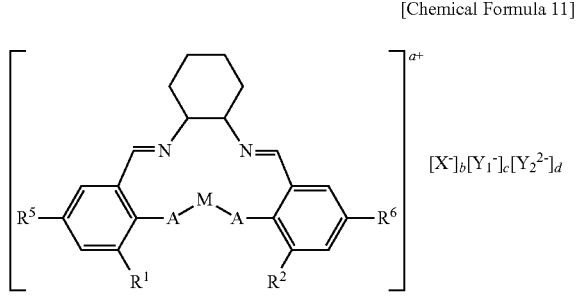

[Chemical Formula 12]

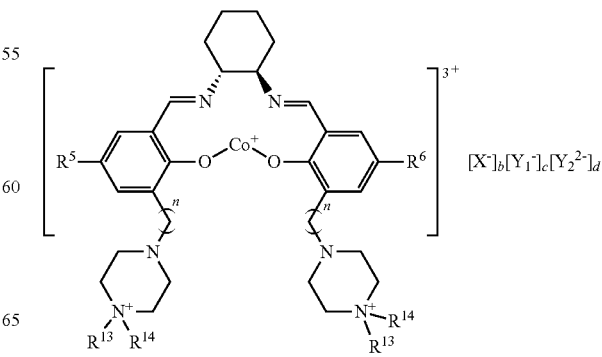

[Chemical Formula 13]
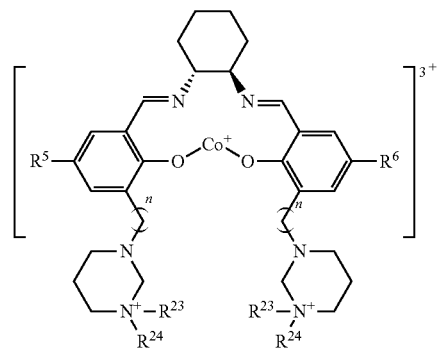
[Chemical Formula 14]
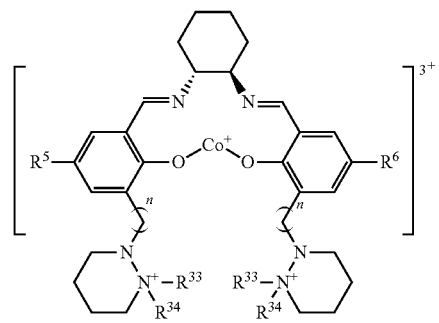
[Chemical Formula 15]
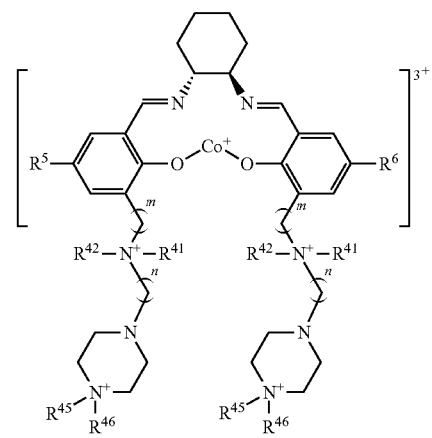
[Chemical Formula 16]
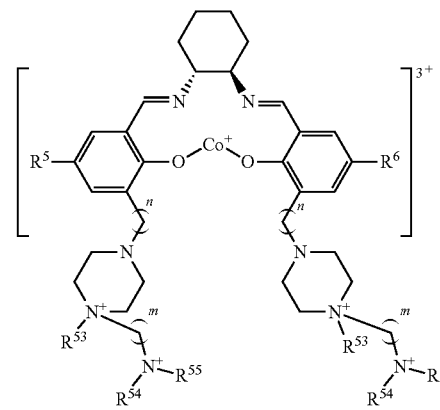
[Chemical Formula 17]
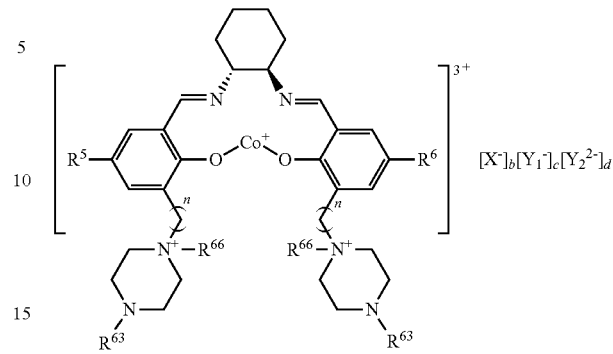
[Chemical Formula 18]
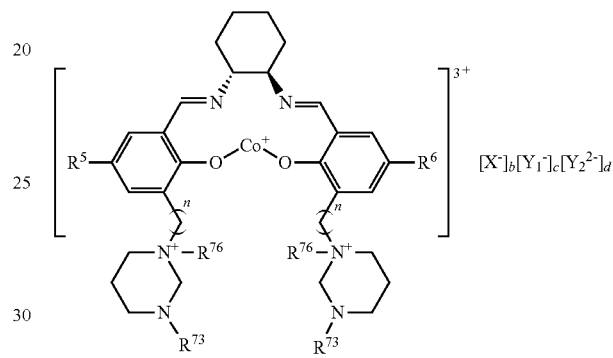
[Chemical Formula 19]
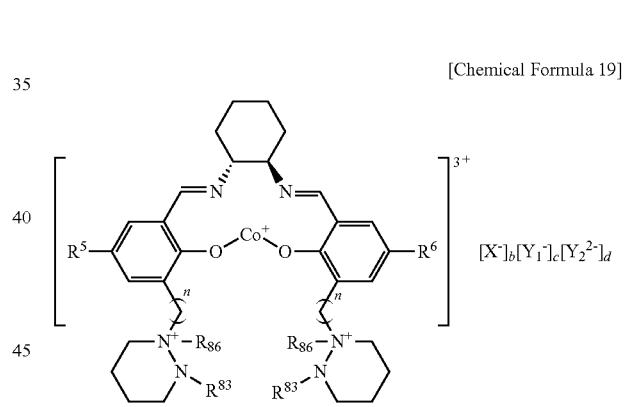
[Chemical Formula 20]
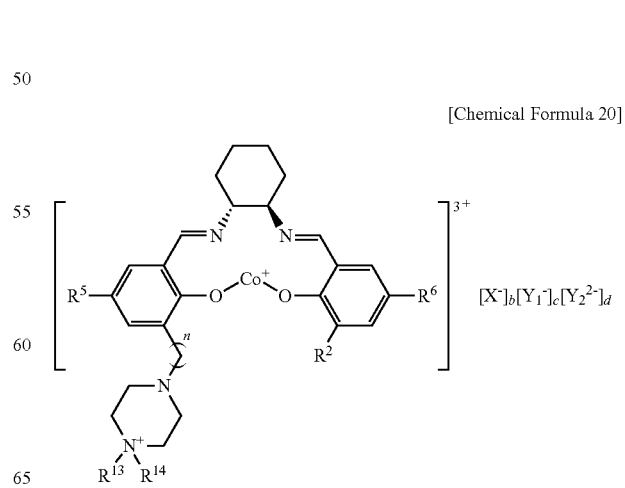

[Chemical Formula 21]

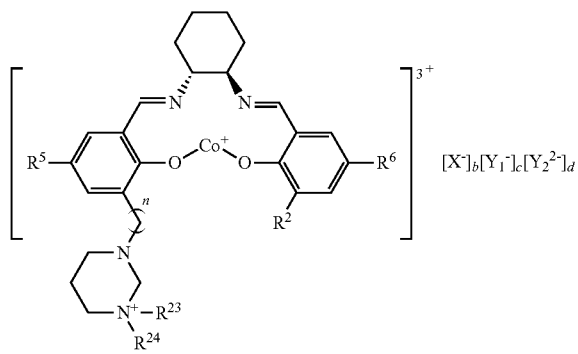

[Chemical Formula 22]

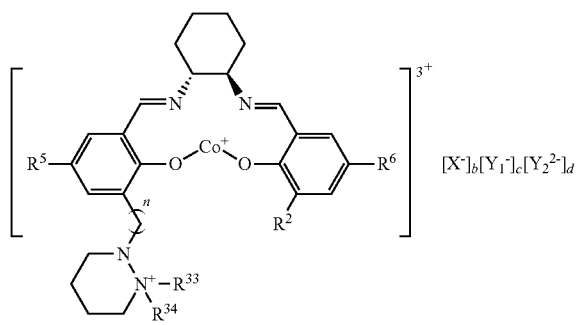

in Chemical Formulas 12 to 22,
$R^2$ is hydrogen or (C1-C20)alkyl;
$R^5$ or $R^6$ is hydrogen, halogen, (C1-C10)alkyl or (C1-C10)alkoxy;
$R^{13}$, $R^{14}$, $R^{23}$, $R^{24}$, $R^{33}$, $R^{34}$, $R^{41}$, $R^{42}$, $R^{45}$, $R^{46}$, $R^{53}$, $R^{54}$, $R^{55}$, $R^{63}$, $R^{66}$, $R^{73}$, $R^{76}$, $R^{83}$ and $R^{86}$ are each independently (C1-C10)alkyl;
m or n is each independently an integer of 1 to 10;
$X^-$ is $Cl^-$, an acetate anion ($CH_3COO^-$) or a 4-nitrophenoxy anion ($NO_2$—$C_6H_5O^-$);
$X^-$ may be coordinated to Co;
$Y_1^-$ is $Cl^-$, $Br^-$ or $NO_3^-$;
$Y_2^{2-}$ is $SO_4^{2-}$ or $CO_3^{2-}$; and
b is an integer of 1 or more, c is an integer of 0 or more, d is an integer of 0 or more, and b+c+2d=3 is satisfied.

More specifically, the complex according to an exemplary embodiment of the present invention may be selected from the following structures, but is not limited thereto:

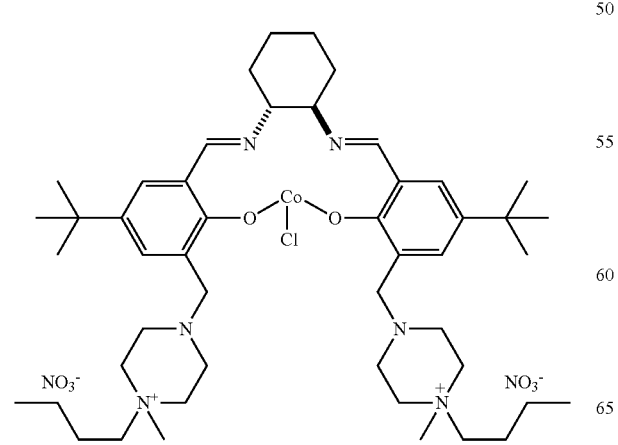

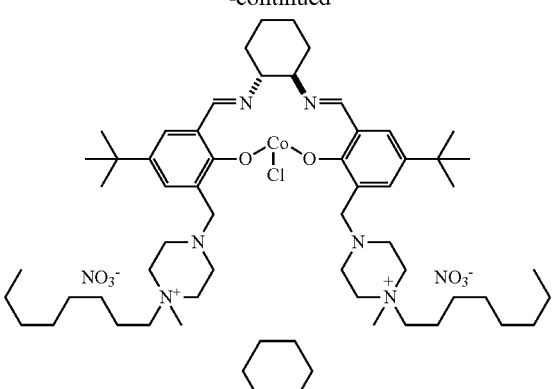

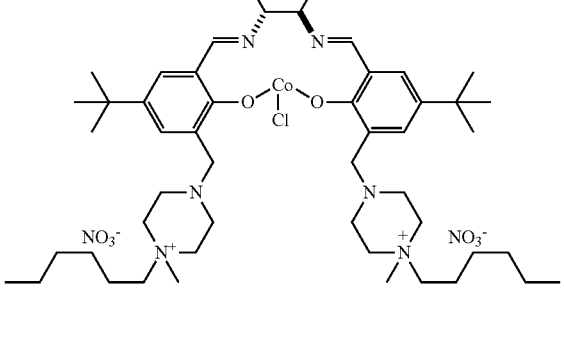

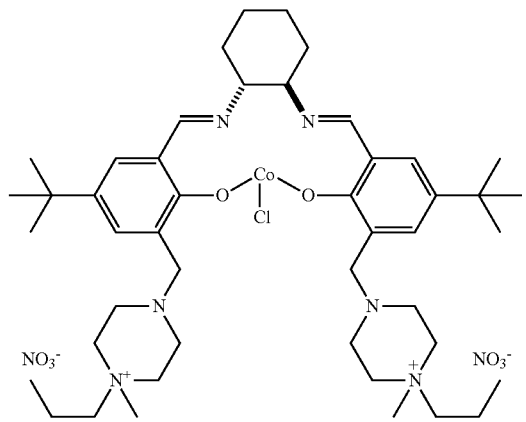

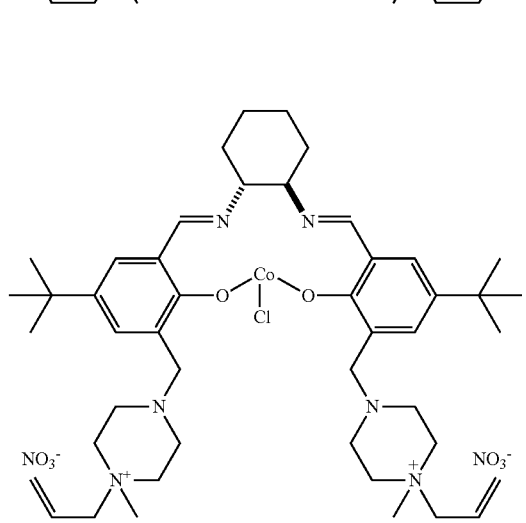

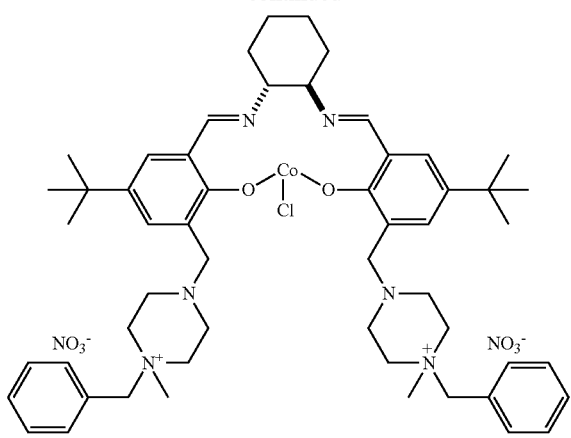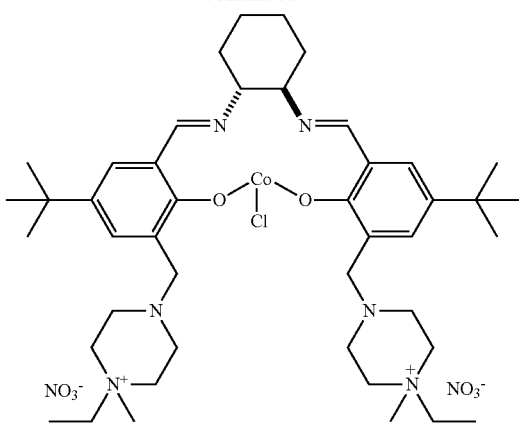

15
-continued
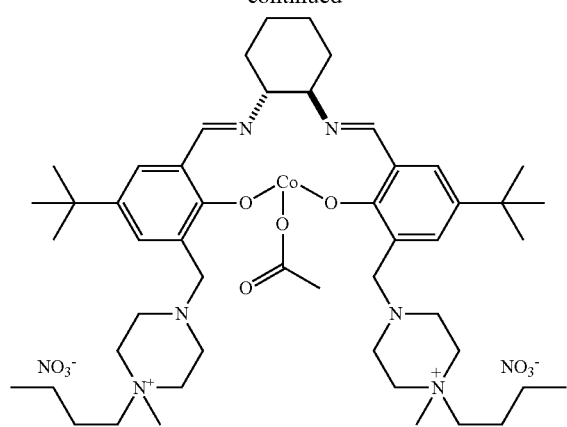
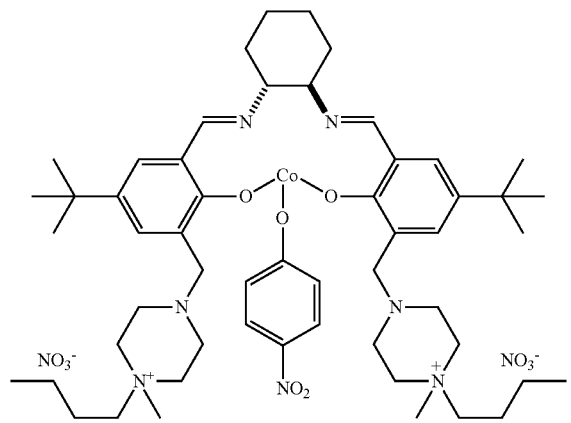
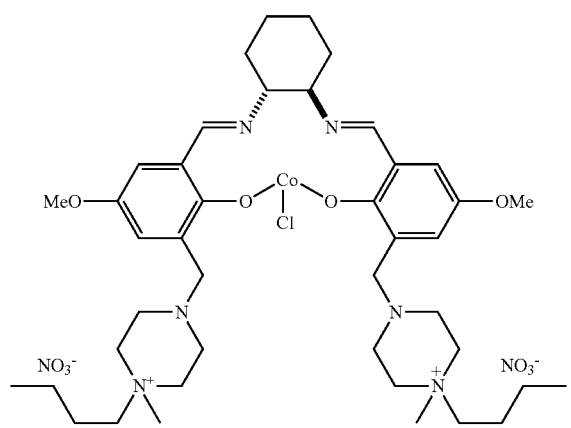
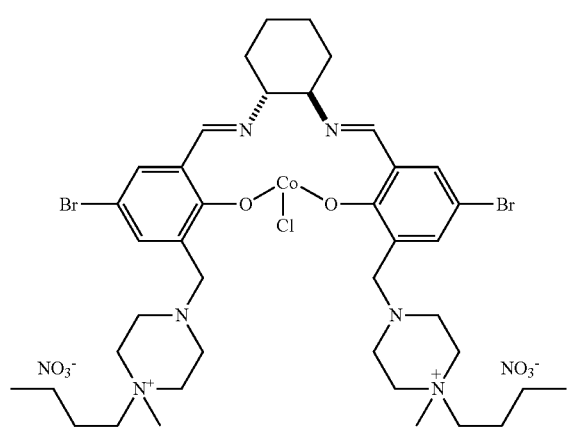
16
-continued
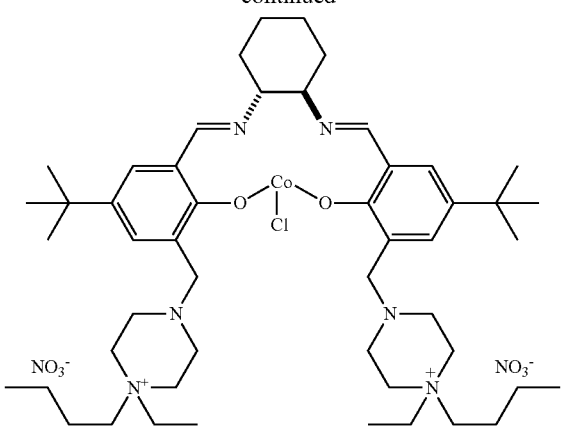
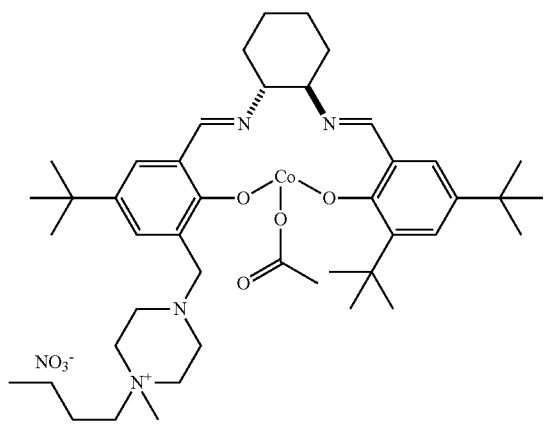
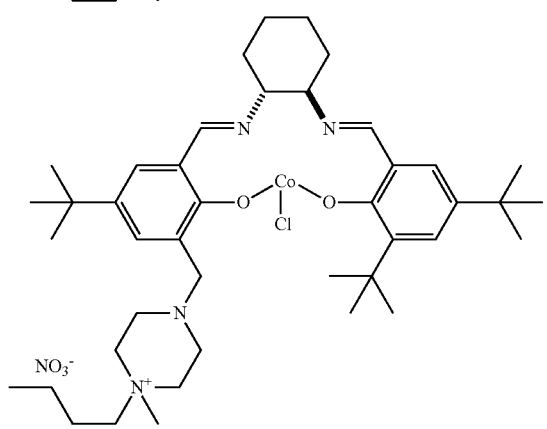
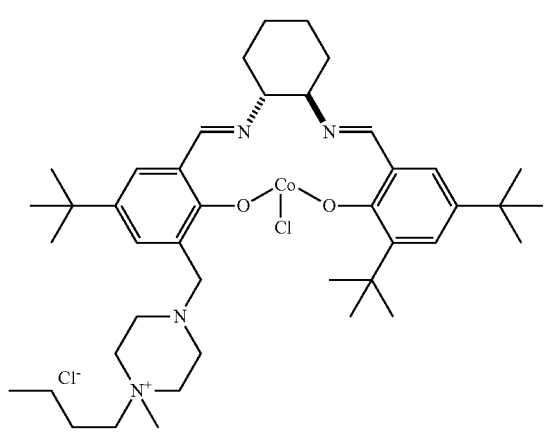

17
-continued
18
-continued
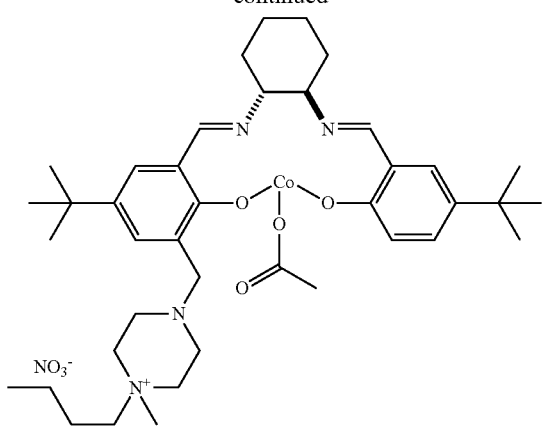
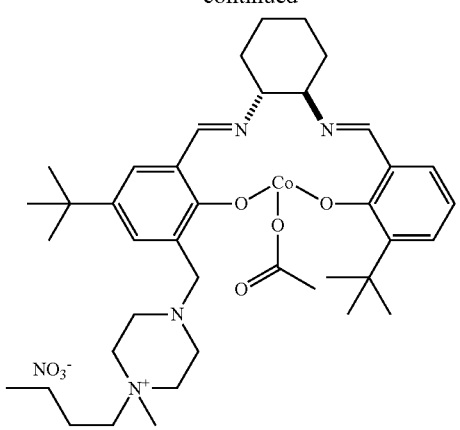

-continued
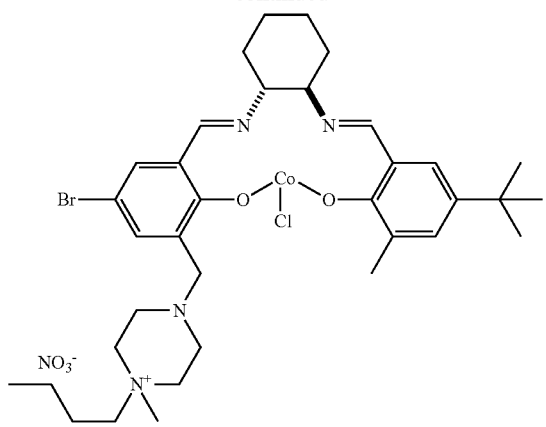
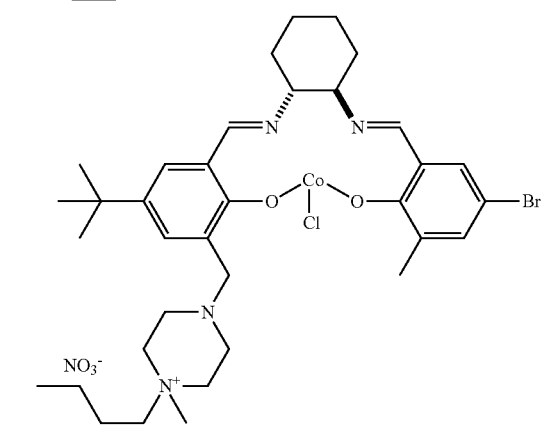
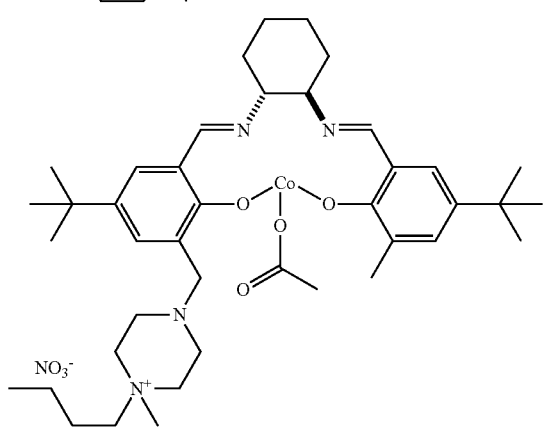
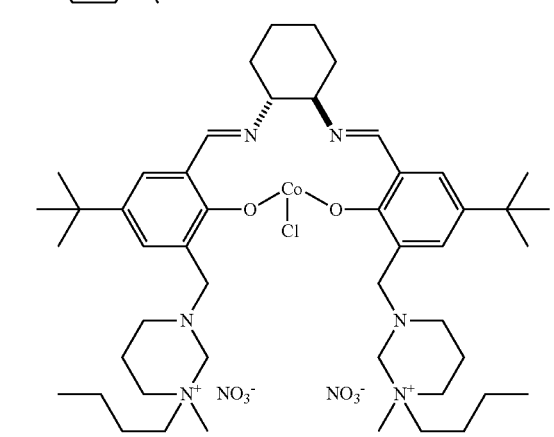
-continued
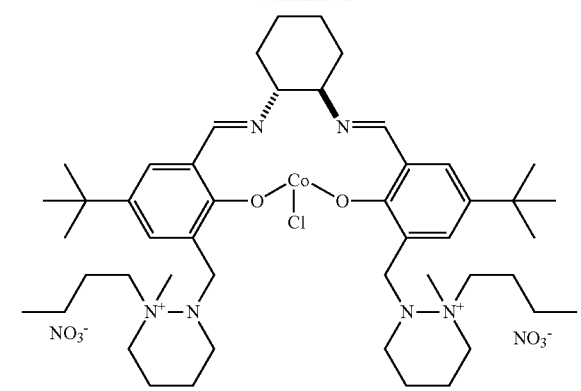
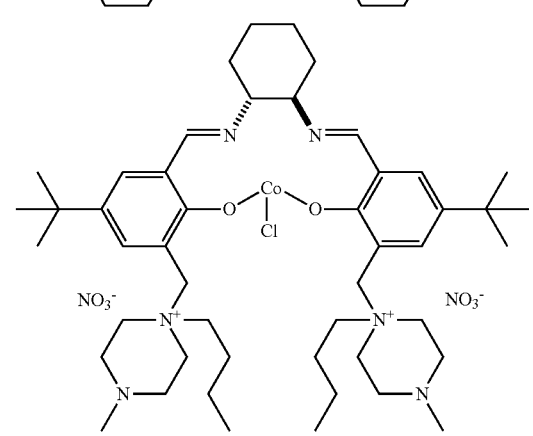
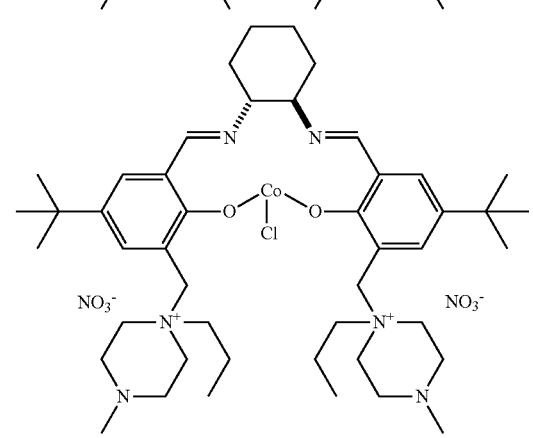
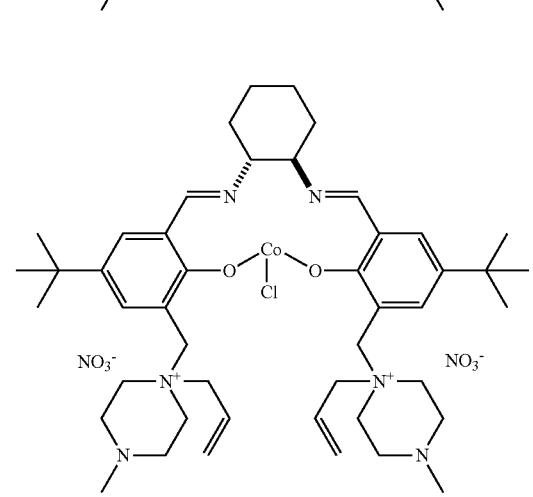

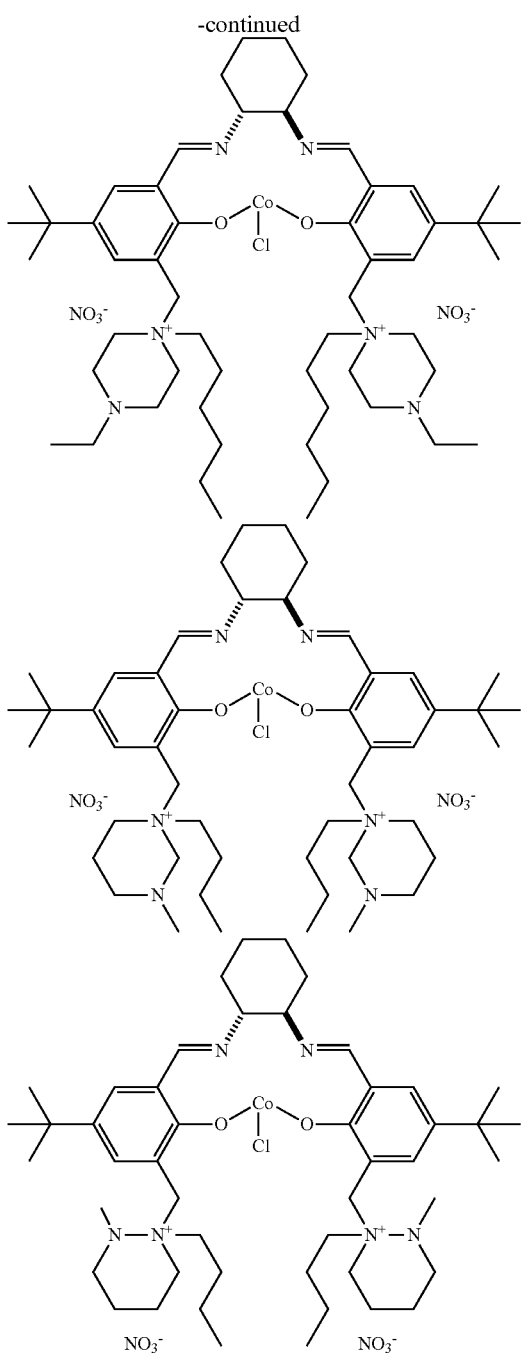

Substituents including "alkyl", "alkoxy" and other "alkyl" parts described in the present invention include both of linear type or branched type. In addition, "aryl" described in the present invention, which is an organic radical derived from aromatic hydrocarbon due to removal of one hydrogen, includes a single ring system or a fused ring system including 4 to 7 ring atoms, preferably, 5 or 6 ring atoms in each ring, and even includes a form in which a plurality of aryls are connected by a single bond. Specific examples of the aryl include phenyl, naphthyl, biphenyl, anthryl, indenyl, fluorenyl, and the like, but the present invention is not limited thereto. "alkenyl" defined in the present invention means a linear-, branched-, or a cyclic hydrocarbon radical containing 2 to 20 carbon atoms and at least one carbon to carbon double bond.

The phrase: "containing one or more of halogen, nitrogen, oxygen, silicon, sulfur and phosphorus" described in the present invention means substituent groups including one or more of halogen, nitrogen, oxygen, silicon, sulfur and phosphorus, and as an example thereof, "an alkyl containing one or more of halogen, nitrogen, oxygen, silicon, sulfur and phosphorus" means an alkyl substituted with substituent groups including one or more of halogen, nitrogen, oxygen, silicon, sulfur and phosphorus. Specifically, haloalkyl, alkoxy and aminoalkyl may be included, but the present invention is not limited thereto.

(C1-C20)alkyl, (C1-C20)alkoxy, and (C3-C20)cycloalkyl according to an exemplary embodiment of the present invention may be preferably (C1-C10)alkyl, (C1-C10) alkoxy, (C3-C12)cycloalkyl; (C6-C20)aryl may be preferably (C6-C12)aryl.

In another general aspect, the present invention provides a preparation method of poly(alkylene carbonate), including: copolymerizing carbon dioxide and one or more epoxide compound selected from a group consisting of (C2-C20) alkylene oxide unsubstituted or substituted with halogen, (C1-C20)alkyloxy, (C6-C20)aryloxy or (C6-C20)ar(C1-C20)alkyl(aralkyl)oxy; (C4-C20)cycloalkylene oxide unsubstituted or substituted with halogen, (C1-C20)alkyloxy, (C6-C20)aryloxy or (C6-C20)ar(C1-C20)alkyl (aralkyl)oxy; and (C8-C20)styrene oxide unsubstituted or substituted with halogen, (C1-C20)alkyloxy, (C6-C20)aryloxy, (C6-C20)ar(C1-C20)alkyl(aralkyl)oxy or (C1-C20) alkyl in the presence of a compound represented by the following Chemical Formula 31 which is a molecular weight regulator, using the complex as described above as a catalyst:

$$J(LH)_c \quad \text{[Chemical Formula 31]}$$

in Chemical Formula 31, J is C1 to C60 hydrocarbyl c-valent radical with or without an ether group, an ester group or an amine group; LH is —OH or —CO$_2$H; and c is an integer from 1 to 10, in which LH may be identical or different when c is 2 or more.

With the preparation method of poly(alkylene carbonate) of the present invention, a molecular weight of the complex and the poly(alkylene carbonate) prepared as a molecular weight regulator represented by Chemical Formula 31 above of the present invention may be regulated, and unlike the related art documents, even though a large amount of molecular weight regulator is used, a catalytic activity may not be deteriorated, such that a preparation amount of poly(alkylene carbonate) may not be decreased.

Therefore, the preparation method of poly(alkylene carbonate) of the present invention may regulate an amount of molecular weight regulator in the presence of the complex of the present invention to be capable of preparing a desired molecular weight of poly(alkylene carbonate). Preferably, in the compound represented by Chemical Formula 31 above which is a molecular weight regulator, a compound in which c is 1; and J is C1 to C60 hydrocarbyl radical with or without an ether group, an ester group, or an amine group may be used as a molecular weight regulator.

Preferably, in the compound represented by Chemical Formula 31, LH may be —OH; and J may be —[CR$_2$]$_n$— (n is an integer of 0 to 20; and R which may be identical or different represents hydrogen, methyl, ethyl, propyl, or butyl).

Preferably, in the compound represented by Chemical Formula 31, a compound in which c is 2; and J is C1 to C60 hydrocarbyl diradical with or without an ether group, an ester group, or an amine group may be used as a molecular weight regulator, and specifically, the compound may be selected from a compound in which the structure of the compound represented by Chemical Formula 31 is $J(CO_2H)_2$ {J is —$[CR_2]_n$— (n is an integer from 0 to 20; and R which may be identical or different represents hydrogen, methyl, ethyl, propyl or butyl), para-phenylene, meta-phenylene, ortho-phenylene or 2,6-naphthalenediyl}, or a compound in which the structure of the compound represented by Chemical Formula 31 is $J(OH)_2$ {J is —$[CR_2]_n$— (n is an integer from 0 to 20; and R which may be identical or different represents hydrogen, methyl, ethyl, propyl or butyl), —$CH_2CH_2N(R)CH_2CH_2$— (R is C1-C20 hydrocarbyl), or —$[CH_2CH(R)O]_nCH_2$ $CH(R)$— (n is an integer from 0 to 10; and R is hydrogen or methyl)}, or a compound in which the structure of the compound represented by Chemical Formula 31 is OH—$C_6H_4$—$CO_2H$.

In addition, in the compound represented by Chemical Formula 31, a compound in which c is 3; and J is a C1-C60 hydrocarbyl triradical with or without an ether group, an ester group or an amine group may be used as a molecular weight regulator, and specifically, an example of the compound may include a compound in which the structure of the compound represented by Chemical Formula 31 is $J(CO_2H)_3$ (J is 1,2,3-propanetriyl, 1,2,3-benzenetriyl, 1,2,4-benzenetriyl or 1,3,5-benzenetriyl.

Further, in the compound represented by Chemical Formula 31, a compound in which c is 4; and J is a C1-C60 hydrocarbyl tetraradical with or without an ether group, an ester group or an amine group may be used as a molecular weight regulator, and specifically, an example of the compound may include a compound in which the structure of the compound represented by Chemical Formula 31 is $J(CO_2H)_4$ (1,2,3,4-butanetetrayl or 1,2,4,5-benzenetetrayl).

In addition, specific examples of the compound represented by Chemical Formula 31 may include adipic acid, ethanol, caproic acid, succinic acid, ethylene glycol, diethylene glycol, N-phenyl diethanol amine, 4-hydroxybenzoic acid, 1,2,3-propane tricarboxylic acid, 1,2,4-benzene tricarboxylic acid or 1,2,3,4-butanetetracarboxylic acid, and the like.

Specific examples of the epoxide compound in the preparation method according to the present invention include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxide-7-octene, epifluorohydrin, epichlorohydrin, epibromohydrin, isopropyl glycidyl ether, butyl glycidyl ether, tert-butyl glycidyl ether, 2-ethylhexyl glycidyl ether, allyl glycidyl ether, cyclopentene oxide, cyclohexene oxide, cyclooctene oxide, cyclododecene oxide, alpha-pinene oxide, 2,3-epoxidenorbomene, limonene oxide, dieldrin, 2,3-epoxidepropylbenzene, styrene oxide, phenylpropylene oxide, stilbene oxide, chlorostilbene oxide, dichlorostilbene oxide, 1,2-epoxy-3-phenoxypropane, benzyloxymethyl oxyrane, glycidyl-methylphenyl ether, chlorophenyl-2,3-epoxidepropyl ether, epoxypropyl methoxy phenyl ether, biphenyl glycidyl ether, glycidyl naphthyl ether, and the like.

The epoxide compound may be used in polymerization using an organic solvent as a reaction medium, and examples of the solvent include aliphatic hydrocarbons such as pentane, octane, decane, cyclohexane, and the like, aromatic hydrocarbons such as benzene, toluene, xylene, and the like, and halogenated hydrocarbons such as chloromethane, methylene chloride, chloroform, carbon tetrachloride, 1,1-dichloroethane, 1,2-dichloroethane, ethylchloride, trichloroethane, 1-chloropropane, 2-chloropropane, 1-chlorobutane, 2-chlorobutane, 1-chloro-2-methylpropane, chlorobenzene, bromobenzene, and the like, which may be used alone or in combination of two or more thereof. More preferably, bulk polymerization using a monomer itself as a solvent may be performed.

In the preparation method of the present invention, a molar ratio of the epoxide compound to catalyst may range from 500 to 1,000,000, preferably from 1,000 to 300,000. In addition, a molar ratio of the catalyst to the molecular weight regulator may range from 1 to 3,000, preferably from 5 to 2,000. In the preparation method of the present invention, pressure of carbon dioxide may be up to 100 bar, preferably, 5 bar to 50 bar. In the preparation method of the present invention, polymerization temperature may be from 10° C. to 120° C., preferably, 20° C. to 90° C.

The poly(alkylene carbonate) prepared by the preparation method of the present invention has a number average molecular weight ($M_n$) of 1,000 to 500,000 and a molecular weight distribution (that is, $M_w/M_n$, PDI) of 1.0 to 3.0. Here, $M_n$ indicates a number average molecular weight measured by GPC with calibration using polystyrene having a single molecular weight distribution as a standard material, and molecular weight distribution $M_w/M_n$ indicates a ratio between a weight average molecular weight and a number average molecular weight specified by GPC using the same method.

Meanwhile, since the preparation method of the present invention is characterized by using the novel complex as the catalyst, as another embodiment of the present invention, poly(alkylene carbonate) having a high molecular weight may be prepared by copolymerization of carbon dioxide and epoxide only in the presence of the novel complex without addition of the molecular weight regulator, and a combination of the novel complex and the molecular weight regulator represented by Chemical Formula 31 above of the present invention may regulate a molecular weight, such that poly(alkylene carbonate) having a high molecular weight as well as a low molecular weight may be prepared.

The maximum turnover number (TON) which is capable of being implemented by the catalyst used in the preparation method of the present invention is about 10,000 or more.

The poly(alkylene carbonate) prepared by the preparation method of the present invention may be preferably represented by the following Chemical Formula 41, and here, the —OH terminal group may be used to prepare polyurethane:

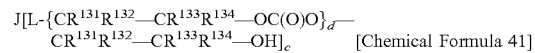
[Chemical Formula 41]

in Chemical Formula 41,

L is —O— or —$CO_2$—;

c is an integer of 2 to 10, L may be identical or different;

J is C1-C60 hydrocarbyl c-valent radical with or without an ether group, an ester group or an amine group;

$R^{131}$ to $R^{134}$ are each independently hydrogen; (C1-C10) alkyl unsubstituted or substituted with halogen or (C1-C20) alkoxy; (C6-C12)aryl unsubstituted or substituted with halogen or (C1-C20)alkoxy and may be linked with each other to thereby form a ring; and a value obtained by multiplying d by c is a natural number of 1000 or less.

In other words, in the polymer compound represented by Chemical Formula 41, c is 2; J is C1-C60 hydrocarbyl diradical with or without an ether group, an ester group or an amine group; $R^{131}$ to $R^{134}$ are each independently hydrogen or methyl; d is an integer of 5 to 500, and preferably, all of $R^{131}$ to $R^{134}$ may be hydrogen or all of $R^{131}$ to $R^{133}$ may be hydrogen and $R^{134}$ may be methyl(in some repeated units, $R^{131}$ is methyl, and all of the remaining $R^{132}$ to $R^{134}$ are hydrogen).

The polymer compound represented by Chemical Formula 41 may be preferably a compound in which c is 2; L is —$CO_2$—; J is —$[CR_2]_n$— (n is an integer of 0 to 20; R which may be identical or different represents hydrogen, methyl, ethyl, propyl or butyl), para-phenylene, meta-phenylene, ortho-phenylene or 2,6-naphthalenediyl, or a compound in which c is 2; L is —O—; J is —$[CR_2]_n$— (n is an integer of 0 to 20; R which may be identical or different represents hydrogen, methyl, ethyl, propyl or butyl), —$CH_2CH_2N(R)CH_2CH_2$— (R is C1 to C20 hydrocarbyl) or —$[CH_2CH(R)O]_nCH_2CH(R)$— (n is an integer of 0 to 10; and R is hydrogen or methyl).

In other words, in the polymer compound represented by Chemical Formula 41, c is 3; J is C1-C60 hydrocarbyl diradical with or without an ether group, an ester group or an amine group; $R^{131}$ to $R^{134}$ are each independently hydrogen or methyl; d is a natural number of 330 or less, and preferably, all of $R^{131}$ to $R^{134}$ may be hydrogen or all of $R^{131}$ to $R^{133}$ may be hydrogen and $R^{134}$ may be methyl(in some repeated units, $R^{131}$ is methyl, and all of the remaining $R^{132}$ to $R^{134}$ are hydrogen).

The polymer compound represented by Chemical Formula 41 is preferably a compound in which c is 3; L is —$CO_2$—; and J is 1,2,3-propanetriyl, 1,2,3-benzenetriyl, 1,2,4-benzenetriyl or 1,3,5-benzenetriyl.

In other words, in the polymer compound represented by Chemical Formula 41, c is 4; J is C1-C60 hydrocarbyl diradical with or without an ether group, an ester group or an amine group; $R^{131}$ to $R^{134}$ are each independently hydrogen or methyl; d is a natural number of 250 or less, and preferably, all of $R^{131}$ to $R^{134}$ may be hydrogen or all of $R^{131}$ to $R^{133}$ may be hydrogen and $R^{134}$ may be methyl(in some repeated units, $R^{131}$ is methyl, and all of the remaining $R^{132}$ to $R^{134}$ are hydrogen).

The polymer compound represented by Chemical Formula 41 is preferably a compound in which c is 4; L is —$CO_2$—; and J is 1,2,3,4-butanetetrayl or 1,2,4,5-benzenetetrayl.

In the case where the polymer compound in which c is 3 or 4, which is a star shaped polymer having three or four branches, is used to prepare polyurethane, it may induce cross-linking and thus may be employed in preparation of thermosetting polyurethane.

Poly(alkylene carbonate) polymer prepared by the preparation method of the present invention may be used itself as a coating material, and the like, and may also be used in a blend with other polymers.

Advantageous Effects of Invention

The novel complex of the present invention structurally includes at least one or more onium salts in a molecule, and more specifically, includes at least one or more structures containing an amine functional group and an onium salt or containing phosphine or an onium salt, in a molecule, such that the complex used as a catalyst may have significantly excellent activity and promote polymerization even at a relatively low temperature. In addition, as compared to the existing copolymerization catalyst, the novel complex of the present invention has a simple structure to be capable of being effectively prepared by a simple process, such that it is expected that the novel complex may be effectively applied to a large-scale commercial process due to the economical preparation cost thereof.

Further, according to the present invention, poly(alkylene carbonate) having a low molecular weight may be prepared by copolymerization of carbon dioxide/epoxide using the molecular weight regulator in the presence of the novel complex, and even though the molecular weight regulator is used, the catalytic activity may be stably maintained, such that poly(alkylene carbonate) having a desirable level of molecular weight may be effectively provided and poly(alkylene carbonate) having a high molecular weight may also be prepared using a small amount of molecular weight regulator.

In addition, it is expected that the poly(alkylene carbonate) prepared by the preparation method of the present invention may also be effectively used even in preparing polyurethane.

MODE FOR THE INVENTION

Hereinafter, the following Examples and Comparative Examples specifically describe the effect of the present invention. However, Examples below are not intended to limit the scope of the present invention but are only for exemplifying the present invention.

PREPARATION EXAMPLE 1

A cobalt-Salen catalyst 6 was prepared by the following Reaction Formula 1:

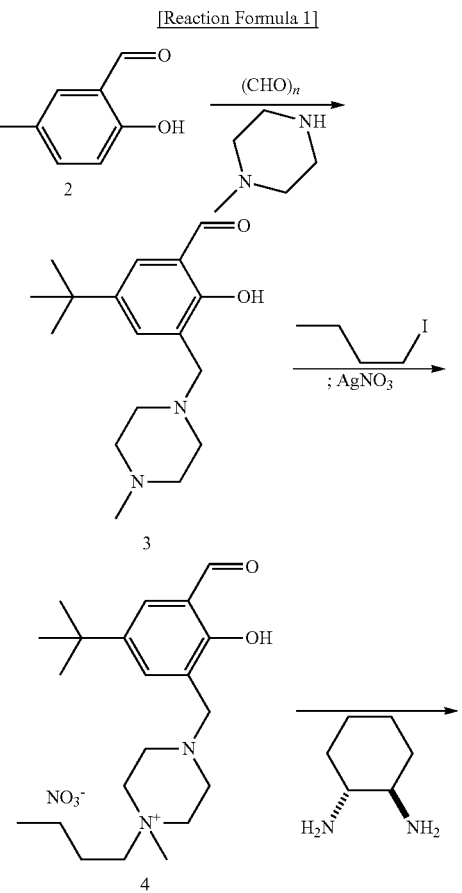

[Reaction Formula 1]

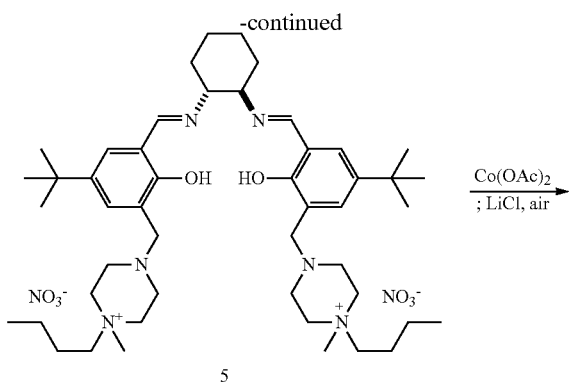

5

6

Paraformaldehyde (0.7 g) and N-methylpiperazine (2.6 mL) were dissolved into acetonitrile (40 mL), and salicylaldehyde 2 (3.4 g) was added thereinto and stirred at 80° C. for 10 hours. When the reaction was completed, a saturated ammonium chloride aqueous solution was added thereinto to terminate the reaction, and the reactant was extracted with dichloromethane three times. An organic layer was separated and dried by magnesium sulfate, followed by filtration and distillation under reduced pressure to remove a solvent and obtain salicylaldehyde 3 containing piperazine (5.5 g). The prepared salicylaldehyde derivative 3 (3.6 g) was added into a round bottom flask wrapped with aluminum foil and was dissolved into acetonitrile (25 mL) and then 1-iododebutane (1.8 mL) was added thereinto, followed by stirring at 80° C. for 8 hours. A solvent was removed by distillation under reduced pressure, the reactant was dissolved into dichloromethane (19 mL) and silver nitrate (1.8 g) was added thereinto, followed by stirring at room temperature for 6 hours. After the reaction solution was filtered when the reaction was completed, a solvent was removed by distillation under reduced pressure to obtain a salicylaldehyde derivative 4 containing amine and an ammonium salt (3.3 g). The salicylaldehyde derivative 4 (2.7 g) containing amine and an ammonium salt and 1,2-trans-diaminocyclohexane (0.5 mL) were dissolved into dichloromethane (13 mL), followed by stirring at room temperature for 2 hours. When the reaction was completed, a solvent was removed by distillation under reduced pressure and dried to obtain a Salen derivative 5 (2.9 g). The prepared ligand 5 (0.5 g) was dissolved into dichloromethane (2 mL), and cobalt acetate tetrahydrate (144 mg) was added thereinto, followed by stirring at room temperature for 12 hours, and then lithium chloride (25 mg) was added thereinto and the reactant was oxidized by air. The produced metal complex was dissolved into dichloromethane again, an organic layer was extracted with water, and impurities were removed. After distillation under reduced pressure, a cobalt-Salen catalyst 6 containing amine and an ammonium salt (0.3 g) was obtained. Result obtained by spectroscopy experiment of the Salen derivative 5 containing amine and an ammonium salt was as follows.

$^1$H NMR (500 MHz, CDCl$_3$)d 13.55 (2H, br s), 8.32 (2H, s), 7.26 (2H, s), 7.14 (2H, s), 3.58-3.55 (2H, d, J=15.0 Hz), 3.50 (6H, m), 3.46 (8H, m), 3.35 (2H, m), 3.21 (6H, s), 2.93-2.87 (4H, m), 2.84-2.78 (4H, m), 1.86-1.81 (4H, m), 1.76 (4H, m), 1.45-1.35 (8H, m), 1.25 (18H, s), 0.97-0.95 (6H, t, J=7.5 Hz)

PREPARATION EXAMPLE 2

A cobalt-Salen catalyst 9 was prepared by the following Reaction Formula 2:

[Reaction Formula 2]

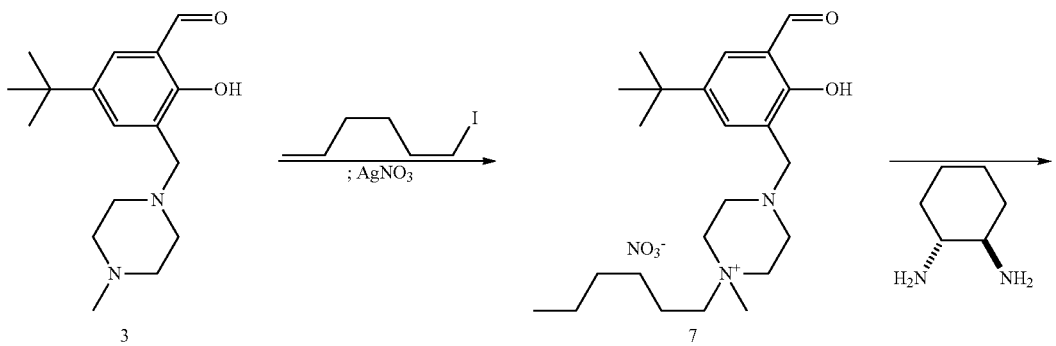

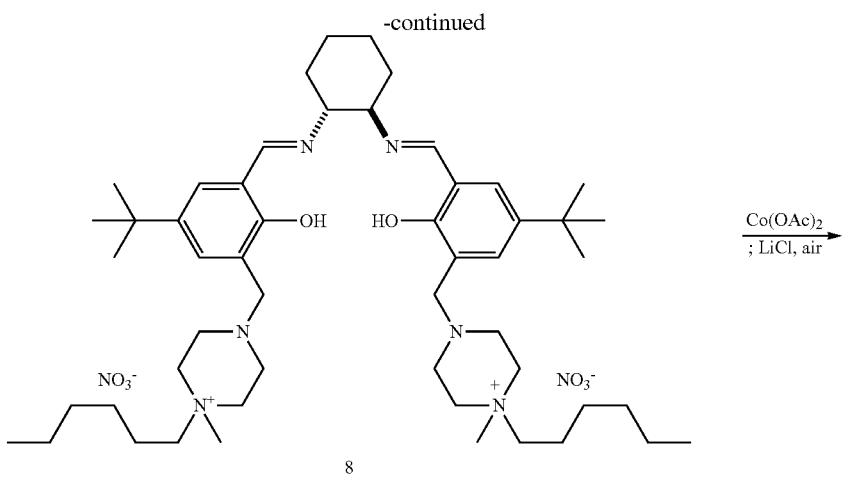

8

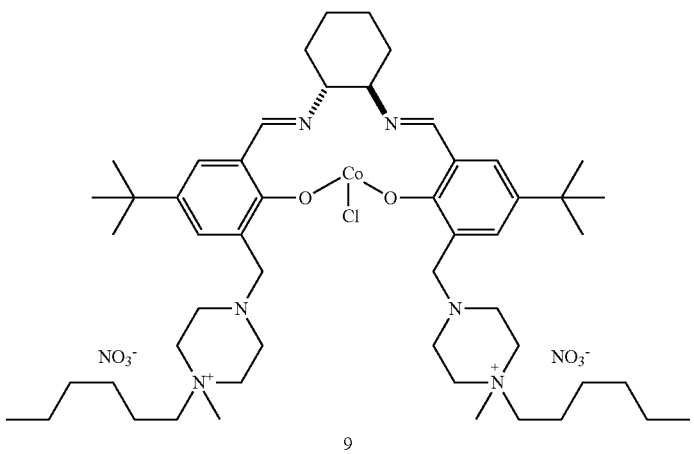

9

The salicylaldehyde derivative 3 (0.5 g) prepared by the same method as Preparation Example 1 above was added into a round bottom flask wrapped with aluminum foil and was dissolved into acetonitrile (10 mL) and then 1-bromohexane (0.3 mL) was added thereinto, followed by stirring at 80° C. for 8 hours. A solvent was removed by distillation under reduced pressure, the reactant was dissolved into dichloromethane (10 mL) and silver nitrate (0.25 g) was added thereinto, followed by stirring at room temperature for 6 hours. After the reaction solution was filtered when the reaction was completed, a solvent was removed by distillation under reduced pressure to obtain a salicylaldehyde derivative 7 containing amine and an ammonium salt (0.5 g). The salicylaldehyde derivative 7 containing amine and an ammonium salt (0.5 g) and 1,2-trans-diaminocyclohexane (0.07 mL) were dissolved into dichloromethane (6 mL), followed by stirring at room temperature for 4 hours. A solvent was removed by distillation under reduced pressure, and the reactant was washed with water and dried to obtain a Salen derivative 8 (0.5 g). The prepared ligand 8 (0.5 g) was dissolved into dichloromethane (5 mL), and cobalt acetate tetrahydrate (130 mg) was added thereinto, followed by stirring at room temperature for 12 hours, and then lithium chloride (65 mg) was added thereinto and the reactant was oxidized by air. The produced metal complex was dissolved into dichloromethane again, an organic layer was extracted with water, and impurities were removed. After distillation under reduced pressure, a cobalt-Salen catalyst 9 containing amine and an ammonium salt (0.4 g) was obtained. Result obtained by spectroscopy experiment of the Salen derivative 8 containing amine and an ammonium salt was as follows.

$^1$H NMR (500 MHz, CDCl$_3$) d 13.56 (2H, s), 8.34 (2H, s), 7.27 (2H, s), 7.16 (2H, s), 3.73-3.37 (16H, m), 3.27 (6H, s), 2.87-2.77 (8H, m), 1.95-1.85 (4H, m), 1.74 (8H, s), 1.49-1.43 (2H, m), 1.33-1.29 (4H, m), 1.26 (26H, s), 0.99-0.97 (6H, t, J=9.0 Hz)

PREPARATION EXAMPLE 3

A cobalt-Salen catalyst 12 was prepared by the following Reaction Formula 3:

[Reaction Formula 3]

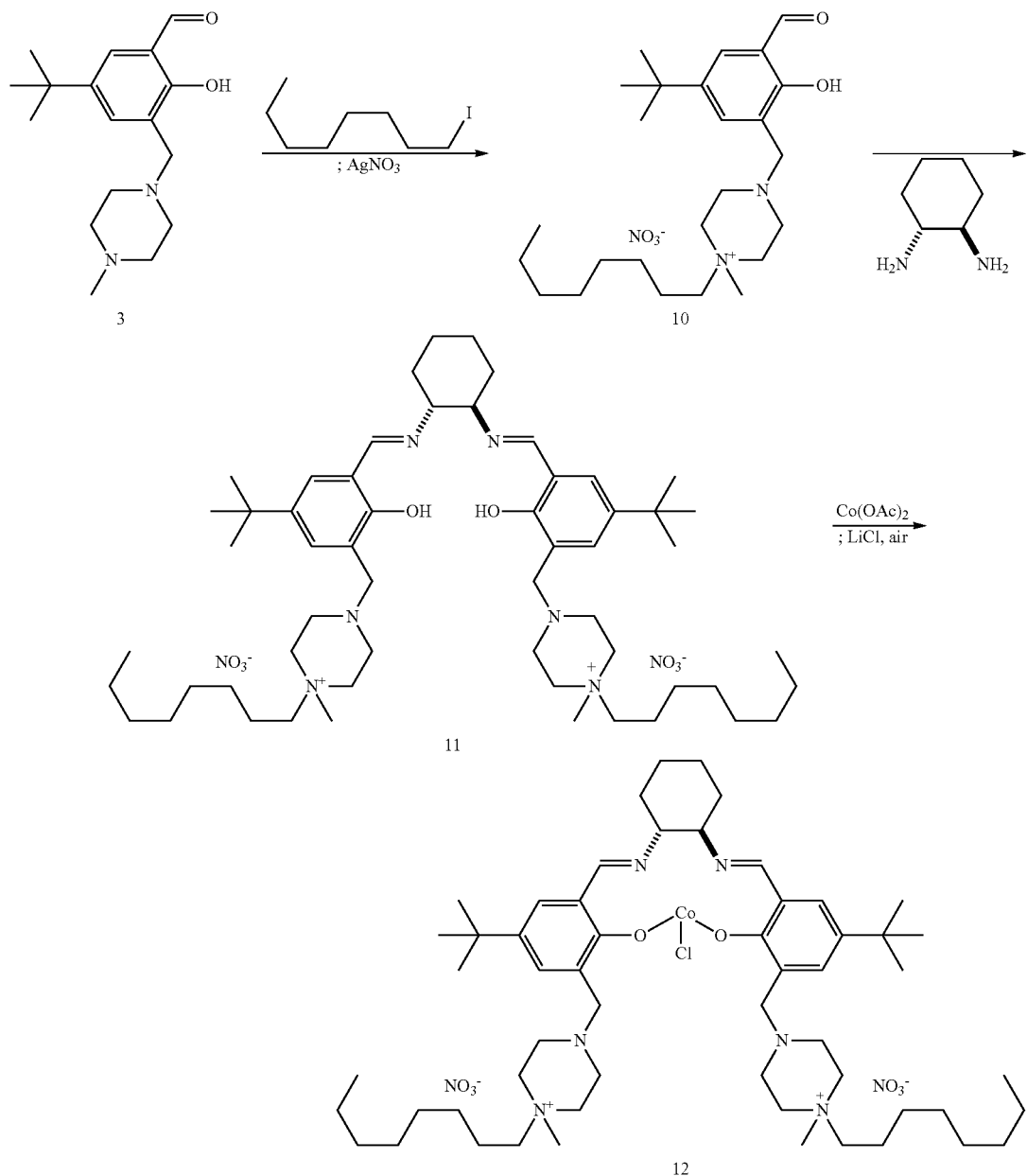

The salicylaldehyde derivative 3 (0.5 g) prepared by the same method as Preparation Example 1 above was added into a round bottom flask wrapped with aluminum foil and was dissolved into acetonitrile (10 mL) and then 1-iodooctane (0.3 mL) was added thereinto, followed by stirring at 80° C. for 10 hours. A solvent was removed by distillation under reduced pressure, the reactant was dissolved into dichloromethane (10 mL) and silver nitrate (0.3 g) was added thereinto, followed by stirring at room temperature for 6 hours. After the reaction solution was filtered when the reaction was completed, a solvent was removed by distillation under reduced pressure to obtain a salicylaldehyde derivative 10 containing amine and an ammonium salt (0.6 g). The salicylaldehyde derivative 10 containing amine and an ammonium salt (0.6 g) and 1,2-trans-diaminocyclohexane (0.07 mL) were dissolved into dichloromethane (6 mL), followed by stirring at room temperature for 4 hours. A solvent was removed by distillation under reduced pressure, and the reactant was washed with water and dried to obtain a Salen derivative 11 (0.3 g). The prepared ligand 11 (0.3 g) was dissolved into dichloromethane (5 mL), and cobalt acetate tetrahydrate (73 mg) was added thereinto, followed by stirring at room temperature for 12 hours, and then lithium chloride (37 mg) was added thereinto and the reactant was oxidized by air. The produced metal complex was dissolved into dichloromethane again, an organic layer was extracted with water, and impurities were removed. After distillation under reduced pressure, a cobalt-Salen catalyst 12 containing amine and an ammonium salt (0.2 g)

was obtained. Result obtained by spectroscopy experiment of the Salen derivative 11 containing amine and an ammonium salt was as follows.

$^1$H NMR (500 MHz, CDCl$_3$) d 13.56 (2H, s), 8.34 (2H, s), 7.26 (2H, s), 7.15 (2H, s), 3.73-3.37 (16H, m), 3.22 (6H, s), 2.84-2.78 (8H, m), 1.93-1.86 (2H, m), 1.71 (8H, s), 1.49-1.43 (2H, m), 1.33-1.27 (24H, m), 1.26 (18H, s), 0.92-0.84 (6H, t, J=8.5 Hz)

PREPARATION EXAMPLE 4

A cobalt-Salen catalyst 15 was prepared by the following Reaction Formula 4:

[Reaction Formula 4]

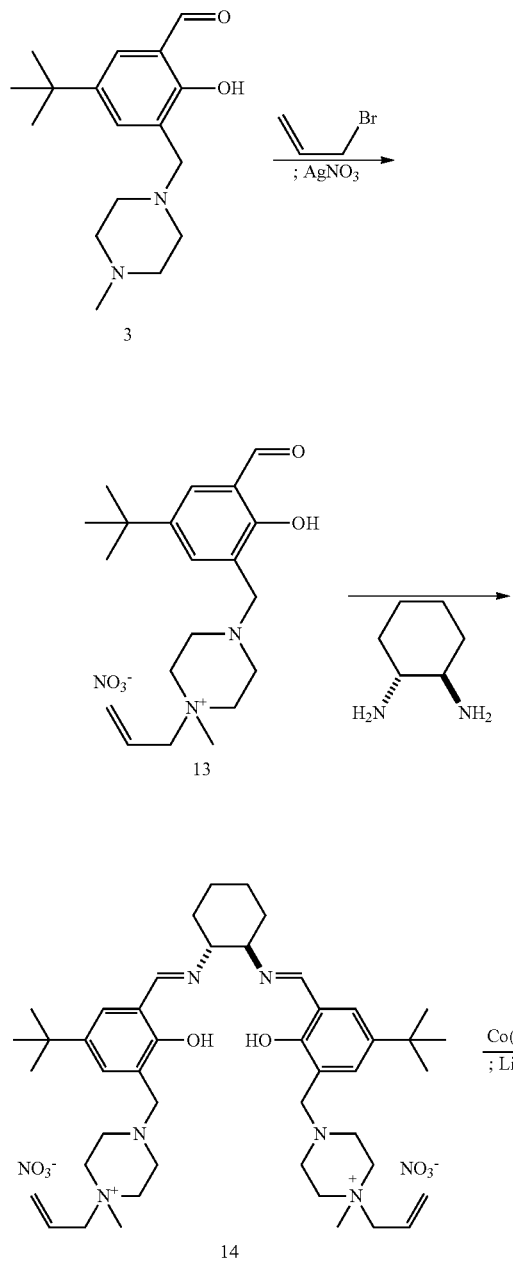

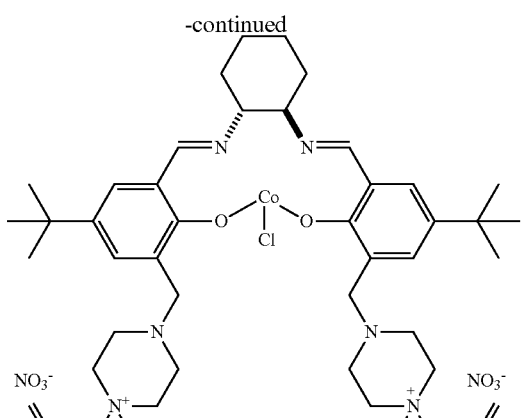

The salicylaldehyde derivative 3 (1.0 g) prepared by the same method as Preparation Example 1 above was added into a round bottom flask wrapped with aluminum foil and was dissolved into acetonitrile (20 mL) and then allyl bromide (0.4 mL) was added thereinto, followed by stirring at 80° C. for 8 hours. A solvent was removed by distillation under reduced pressure, the reactant was dissolved into dichloromethane (20 mL) and silver nitrate (0.7 g) was added thereinto, followed by stirring at room temperature for 6 hours. After the reaction solution was filtered when the reaction was completed, a solvent was removed by distillation under reduced pressure to obtain a salicylaldehyde derivative 13 containing amine and an ammonium salt (1.16 g). The salicylaldehyde derivative 13 containing amine and an ammonium salt (1.2 g) and 1,2-trans-diaminocyclohexane (0.2 mL) were dissolved into dichloromethane (15 mL), followed by stirring at room temperature for 4 hours. A solvent was removed by distillation under reduced pressure when the reaction was completed, and the reactant was washed with water and dried to obtain a Salen derivative 14 (0.7 g). The prepared ligand 14 (0.3 g) was dissolved into dichloromethane (5 mL), and cobalt acetate tetrahydrate (96 mg) was added thereinto, followed by stirring at room temperature for 12 hours, and then lithium chloride (48 mg) was added thereinto and the reactant was oxidized by air. The produced metal complex was dissolved into dichloromethane again, an organic layer was extracted with water, and impurities were removed. After distillation under reduced pressure, a cobalt-Salen catalyst 15 containing amine and an ammonium salt (128 mg) was obtained. Result obtained by spectroscopy experiment of the Salen derivative 14 containing amine and an ammonium salt was as follows.

$^1$H NMR (500 MHz, CDCl$_3$) d 8.34 (2H, s), 7.26 (2H, s), 7.15 (2H, s), 5.95-5.92 (2H, m), 5.81-5.71 (4H, m), 4.19 (4H, d, J=6.5 Hz), 3.65 (4H, s), 3.53 (8H, s), 3.20 (6H, s), 2.95-2.86 (4H, m), 2.82-2.72 (4H, m), 2.01-1.59 (10H, m), 1.28 (18H, s)

PREPARATION EXAMPLE 5

A cobalt-Salen catalyst 18 was prepared by the following Reaction Formula 5:

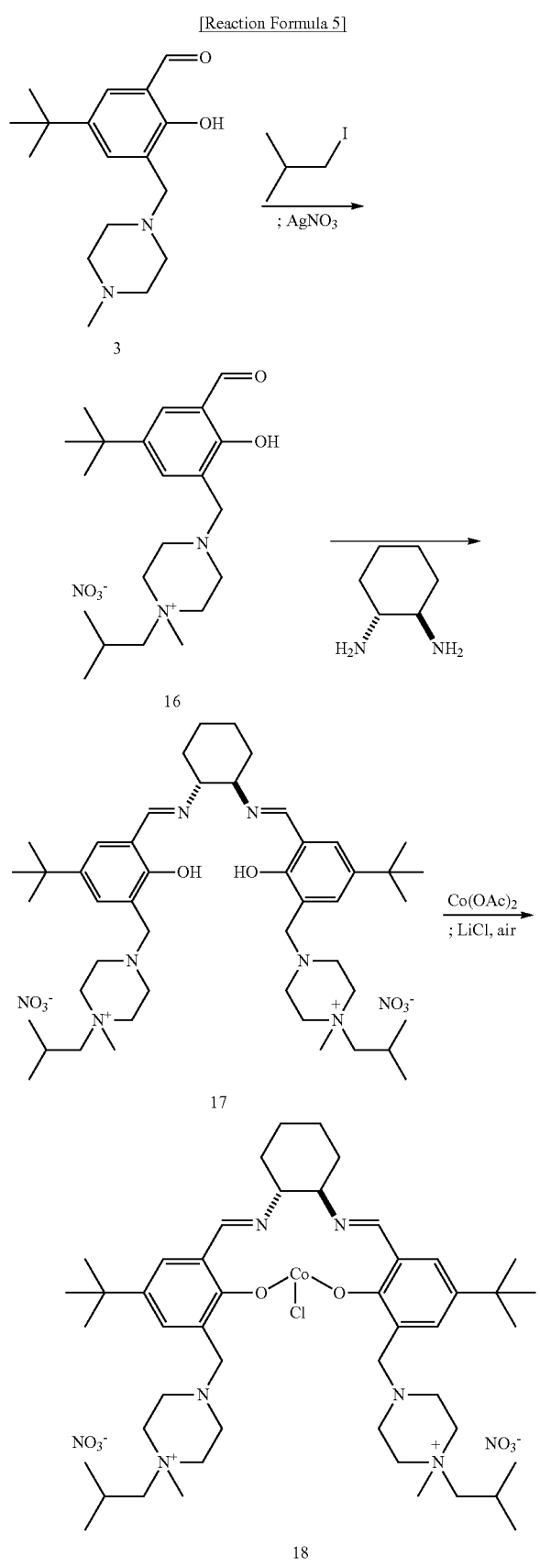

The salicylaldehyde derivative 3 (0.7 g) prepared by the same method as Preparation Example 1 above was added into a round bottom flask wrapped with aluminum foil and was dissolved into acetonitrile (10 mL) and then 1-iodo-2-methylpropane (0.5 mL) was added thereinto, followed by stirring at 80° C. for 8 hours. A solvent was removed by distillation under reduced pressure, the reactant was dissolved into dichloromethane (10 mL) and silver nitrate (0.5 g) was added thereinto, followed by stirring at room temperature for 6 hours. After the reaction solution was filtered when the reaction was completed, a solvent was removed by distillation under reduced pressure to obtain a salicylaldehyde derivative 16 containing amine and an ammonium salt (1.0 g). The salicylaldehyde derivative 16 containing amine and an ammonium salt (1.0 g) and 1,2-trans-diaminocyclohexane (0.2 mL) were dissolved into dichloromethane (10 mL), followed by stirring at room temperature for 4 hours. A solvent was removed by distillation under reduced pressure, and the reactant was washed with water and dried to obtain a Salen derivative 17 (0.7 g). The prepared ligand 17 (0.7 g) was dissolved into dichloromethane (10 mL), and cobalt acetate tetrahydrate (190 mg) was added thereinto, followed by stirring at room temperature for 12 hours, and then lithium chloride (98 mg) was added thereinto and the reactant was oxidized by air. The produced metal complex was dissolved into dichloromethane again, an organic layer was extracted with water, and impurities were removed. After distillation under reduced pressure, a cobalt-Salen catalyst 18 containing amine and an ammonium salt (0.6 g) was obtained. Result obtained by spectroscopy experiment of the Salen derivative 17 containing amine and an ammonium salt was as follows.

$^1$H NMR (500 MHz, CDCl$_3$) d 13.53 (2H, br s), 8.34-8.31 (2H, s), 7.27 (2H, s), 7.15 (2H, s), 3.71-3.37 (16H, m), 3.27 (6H, s) 2.82-2.78 (8H, m), 2.26-2.18 (2H, m), 1.93-1.61 (6H, m), 1.48-1.44 (4H, m), 1.27-1.20 (18H, m), 1.73-1.09 (12H, m)

PREPARATION EXAMPLE 6

A cobalt-Salen catalyst 19 was prepared by the following Reaction Formula 6:

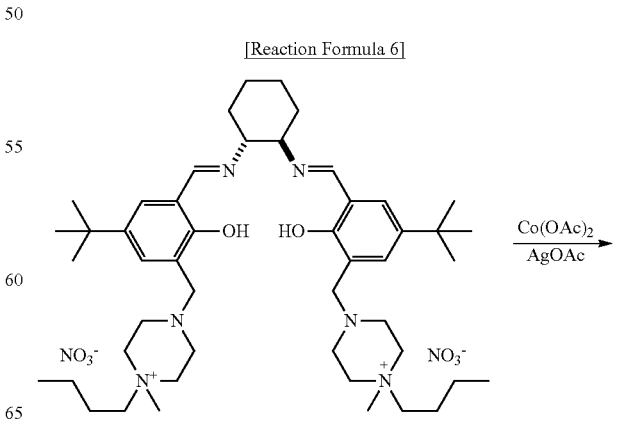

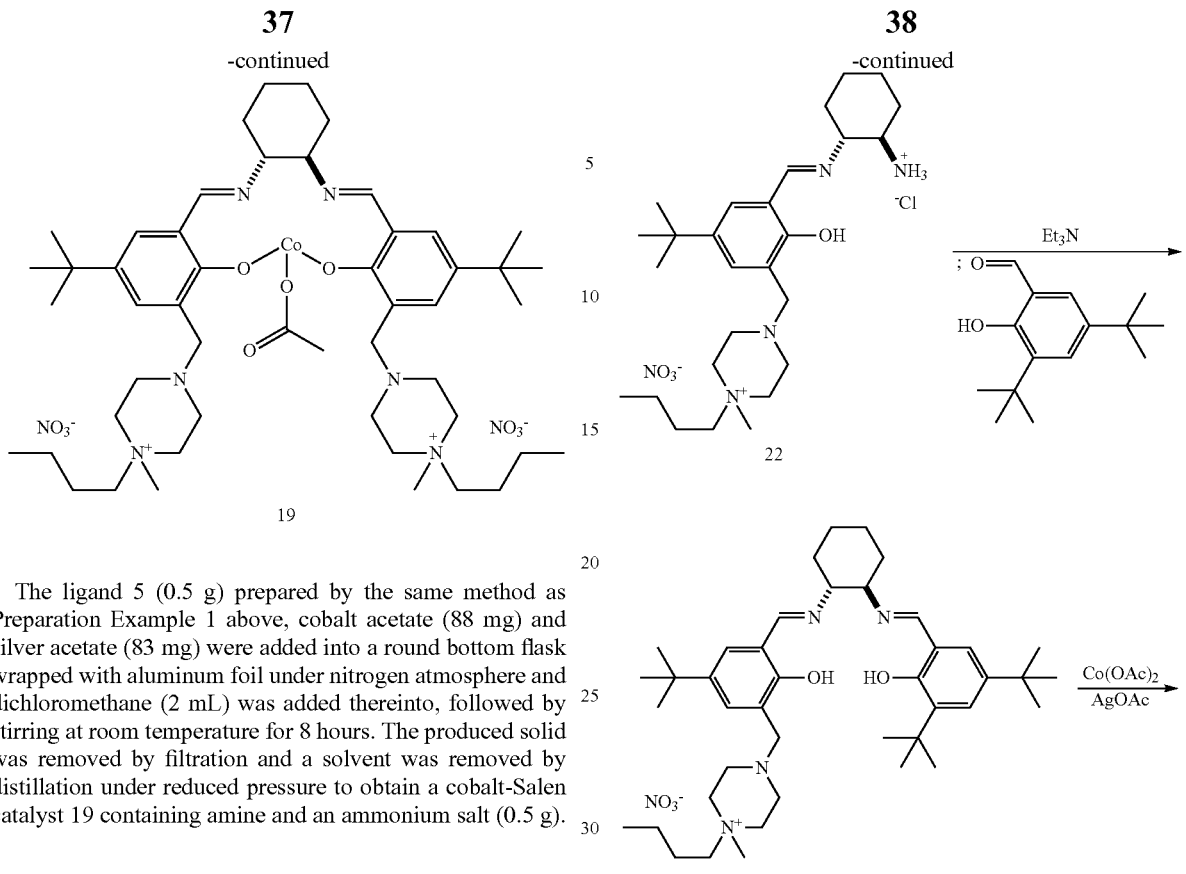

The ligand 5 (0.5 g) prepared by the same method as Preparation Example 1 above, cobalt acetate (88 mg) and silver acetate (83 mg) were added into a round bottom flask wrapped with aluminum foil under nitrogen atmosphere and dichloromethane (2 mL) was added thereinto, followed by stirring at room temperature for 8 hours. The produced solid was removed by filtration and a solvent was removed by distillation under reduced pressure to obtain a cobalt-Salen catalyst 19 containing amine and an ammonium salt (0.5 g).

PREPARATION EXAMPLE 7

A cobalt-Salen catalyst 24 was prepared by the following Reaction Formula 7:

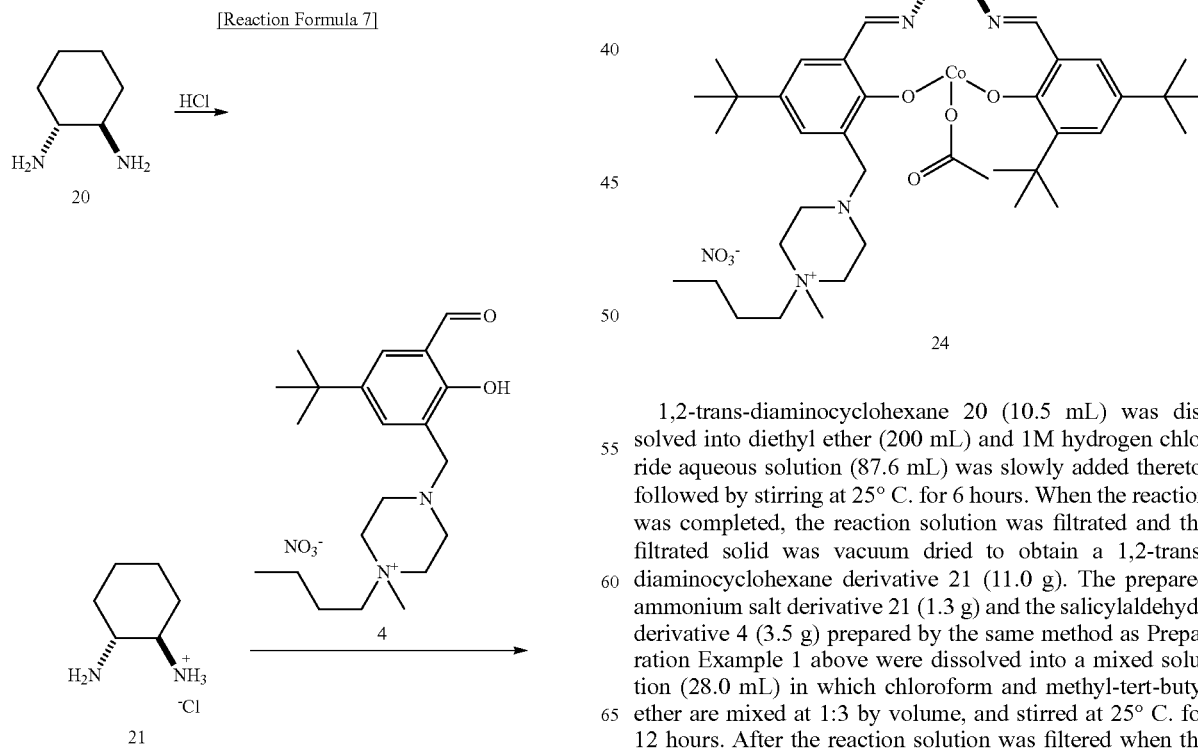

1,2-trans-diaminocyclohexane 20 (10.5 mL) was dissolved into diethyl ether (200 mL) and 1M hydrogen chloride aqueous solution (87.6 mL) was slowly added thereto, followed by stirring at 25° C. for 6 hours. When the reaction was completed, the reaction solution was filtrated and the filtrated solid was vacuum dried to obtain a 1,2-trans-diaminocyclohexane derivative 21 (11.0 g). The prepared ammonium salt derivative 21 (1.3 g) and the salicylaldehyde derivative 4 (3.5 g) prepared by the same method as Preparation Example 1 above were dissolved into a mixed solution (28.0 mL) in which chloroform and methyl-tert-butyl ether are mixed at 1:3 by volume, and stirred at 25° C. for 12 hours. After the reaction solution was filtered when the reaction was completed, the filtrated solid was vacuum dried to obtain a salicylaldehyde derivative 22 containing an ammonium salt (3.1 g). The salicylaldehyde derivative 22 containing amine and an ammonium salt (2.7 g) was dissolved into dimethyl sulfoxide (15.0 mL) and a solution in which 3,5-di-tert-butyl-2-hydroxybenzaldehyde (3.9 g) is dissolved into dimethyl sulfoxide (10.0 mL) was added dropwise at 25° C. for 1 hour. When the reactant was stirred at 25° C. for 12 hours and the reaction was completed, dichloromethane (20.0 mL) was slowly added to the reaction solution to solidify the reactant. The produced solid was filtrated and the filtrated solid was vacuum dried to obtain a Salen derivative 23 (10.7 g). The prepared ligand 23 (1.0 g), cobalt acetate (245 mg) and silver acetate (231 mg) were added into under nitrogen atmosphere and dichloromethane (4 mL) was added thereinto, followed by stirring at room temperature for 6 hours. The produced solid was removed by filtration and a solvent was removed by distillation under reduced pressure to obtain a cobalt-Salen catalyst 24 containing amine and an ammonium salt (1.1 g). Result obtained by spectroscopy experiment of the Salen derivative 23 containing amine and an ammonium salt was as follows.

$^1$H NMR (500 MHz, CDCl$_3$) d 13.55 (2H, br s), 8.40 (1H, s), 8.37 (1H, s), 7.38 (1H, s), 7.26 (1H, s), 7.14 (1H, s), 7.08 (1H, s), 3.58-3.55 (2H, d, J=15.0 Hz), 3.50 (2H, m), 3.46 (2H, m), 3.21 (3H, s), 2.93-2.87 (4H, m), 2.84-2.78 (4H, m), 1.86-1.81 (2H, m), 1.76 (2H, m), 1.45-1.35 (8H, m), 1.44 (9H, s), 1.33 (9H, s), 1.25 (9H, s), 0.97-0.95 (3H, t, J=7.5 Hz)

EXAMPLES 1 to 3

Propylene oxide (PO) and each catalyst were added into a high pressure stainless steel reactor at each molar ratio as shown in the following Table 1 and the reactor was completely fastened. The high pressure reactor was slowly filled with carbon dioxide having ultra-high purity and a subsequent reaction was performed under predetermined pressure, operating temperature and time as shown in the following Table 1. After the reaction was completed, the reactant was cooled and remaining carbon dioxide was slowly discharged. After the catalyst was removed, the reactant was vacuum dried to obtain polycarbonate.

As shown in Table 1, it could be appreciated that in all of Example 1 in which the molecular weight regulator (ethanol) was not used and in Examples 2 and 3 in which the molecular weight regulator in a small amount was used, poly(propylene carbonate) having a high molecular weight was prepared with high selectivity, and in addition, Examples 1 to 3 had high TON, such that productivity of poly(propylene carbonate) was also significantly high.

EXAMPLES 4 to 10

Propylene oxide (PO), each catalyst and diethylene glycol were added into a high pressure stainless steel reactor at each molar ratio as shown in the following Table 2 and the reactor was completely fastened. A solvent was added thereinto as needed. The high pressure reactor was slowly filled with carbon dioxide having ultra-high purity and a subsequent reaction was performed under predetermined pressure, operating temperature and time as shown in the following Table 2. After the reaction was completed, the reaction was cooled and remaining carbon dioxide was slowly discharged. After the catalyst was removed, the reactant was vacuum dried to obtain polycarbonate.

TABLE 2

| Example | Catalyst | PO:Catalyst:Diethylene glycol | CO$_2$ Pressure | Reaction Temperature | Reaction Time | PO Conversion Ratio | Selectivity |
|---|---|---|---|---|---|---|---|
| 4 | 6 | 10,000:1:500 | 30 bar | 50° C. | 8 h | 63% | 99% |
| 5 | 6 | 25,000:1:1,300 | 30 bar | 50° C. | 18 h | 99% | 99% |
| 6 | 9 | 10,000:1:500 | 30 bar | 50° C. | 8 h | 16% | 99% |
| 7 | 12 | 10,000:1:500 | 30 bar | 50° C. | 8 h | 11% | 99% |
| 8 | 15 | 10,000:1:500 | 30 bar | 50° C. | 8 h | 4% | 99% |
| 9 | 18 | 10,000:1:500 | 30 bar | 50° C. | 8 h | 7% | 99% |
| 10 | 19 | 25,000:1:1,300 | 30 bar | 50° C. | 24 h | 99% | 99% |

COMPARATIVE EXAMPLES 1 to 4

Propylene oxide (PO), each binary catalyst system of (Salen)Co compound (combination of the catalyst represented by the following Chemical Formula 23 and PPN$^+$Cl$^-$ represented by the following Chemical Formula 24), and adipic acid were added into a high pressure stainless steel reactor at each molar ratio as shown in the following Table 3 and the reactor was completely fastened. Carbon dioxide having ultra-high purity was slowly filled into the high pressure reactor and reaction was performed under predetermined pressure, operating temperature and time as shown in the following Table 3. After the reaction was completed, the reaction was cooled and remaining carbon dioxide was slowly discharged. After the catalyst was removed, the reactant was vacuum dried to obtain poly(propylene carbonate) and physical properties of the obtained poly(propylene carbonate) were shown in the following Table 4.

TABLE 1

| Example | Catalyst | PO:Catalyst:Ethanol | CO$_2$ Pressure | Reaction Temperature | Reaction Time | Selectivity | M$_w$ (g/mol) | PDI | TON |
|---|---|---|---|---|---|---|---|---|---|
| 1 | 6 | 150,000:1:0 | 35 bar | 65 | 2 h | 99% | 480,000 | 1.4 | 26,000 |
| 2 | 19 | 200,000:1:20 | 35 bar | 65 | 4 h | 99% | 193,000 | 1.15 | 47,500 |
| 3 | 19 | 175,000:1:20 | 35 bar | 65 | 4 h | 99% | 200,000 | 1.14 | 51,700 |

[Chemical Formula 23]

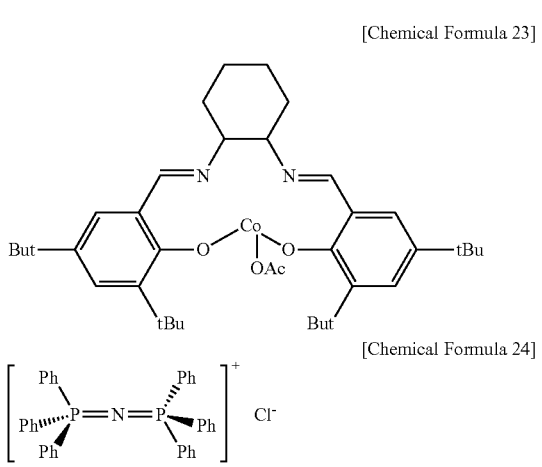

[Chemical Formula 24]

appreciated that even in the case in which the relative equivalent of the molecular weight regulator as compared to the catalyst system was 20 to 1300 which is a general level, PO conversion ratio was obtained as an appropriate value. In particular, it was appreciated that even though the relative equivalent of the molecular weight regulator adopted 10 to 1300 which was a broad range, a low molecular weight of copolymer at an appropriate level was stably provided without a remarkable decrease in the catalytic activity.

In addition, it was appreciated that according to Examples of Table 2, the catalyst of the present invention effectively promoted the reaction even under a relatively low copolymerization temperature condition which was 20° C. to 50° C.

The invention claimed is:
1. A complex represented by the following Chemical Formula 1:

TABLE 3

| Comparative Example | Catalyst | Formula 23:PPN$^+$Cl$^-$:Adipic Acid (Molar Ratio) | CO$_2$ Pressure (bar) | Reaction Temperature (° C.) | Reaction Time (hr) |
|---|---|---|---|---|---|
| 1 | Chemical Formula 23 | 2,000:1:1:0 | 30 | 25 | 6 |
| 2 | Chemical Formula 23 | 2,000:1:1:10 | 30 | 25 | 5 |
| 3 | Chemical Formula 23 | 2,000:1:1:20 | 30 | 25 | 5 |
| 4 | Chemical Formula 23 | 2,000:1:1:30 | 30 | 25 | 5 |

TABLE 4

| Comparative Example | PO Conversion Ratio | Selectivity | $M_n$ | PDI |
|---|---|---|---|---|
| 1 | 93% | 96% | 9,174 | 1.369 |
| 2 | 91% | 100% | 7,973 | 1.156 |
| 3 | <5% | — | — | — |
| 4 | — | — | — | — |

Comparative Examples 1 to 4 above disclose preparation of poly(alkylene carbonate) by copolymerization of carbon dioxide/epoxide using a molecular weight regulator in the presence of the existing binary catalyst system of (Salen)Co compound. It was appreciated from Tables 3 and 4 that as relative equivalent of the molecular weight regulator as compared to the catalyst system is increased, activity of the catalyst system was deteriorated, for example, PO conversion ratio was decreased, and the like. In particular, it was appreciated that in which the relative equivalent of the molecular weight regulator is 20 or more, which is a general level, PO conversion ratio was rapidly decreased to be less than 5%, such that it was determined that activity of the catalyst system was not effectively maintained. Therefore, there is a limitation in obtaining a low molecular weight of copolymer at desirable level by adding the molecular weight regulator at a general quantitative level in the presence of the existing binary catalyst system.

However, according to the preparation method of the present invention disclosed in Examples of Table 2, it was

[Chemical Formula 1]

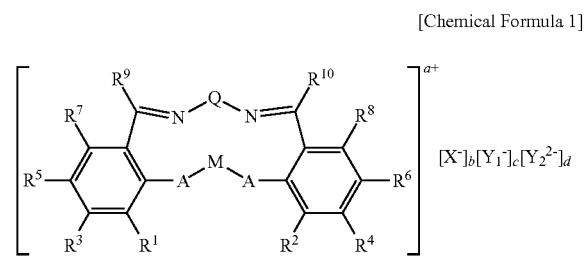

in Chemical Formula 1,
M is trivalent cobalt or trivalent chromium;
A is oxygen or sulfur;
Q is a diradical connecting two nitrogens;
$R^1$ to $R^{10}$ are each independently hydrogen; halogen; (C1-C20)alkyl; (C1-C20)alkyl containing one or more selected from among halogen, nitrogen, oxygen, silicon, a sulfur and phosphorus; (C2-C20)alkenyl; (C2-C20)alkenyl containing one or more selected from among halogen, nitrogen, oxygen, silicon, a sulfur and phosphorus atom; (C1-C20)alkyl(C6-C20)aryl; (C1-C20)alkyl(C6-C20)aryl containing one or more selected from among halogen, nitrogen, oxygen, silicon, a sulfur and phosphorus atom; (C6-C20)aryl(C1-C20)alkyl; (C6-C20)aryl(C1-C20)alkyl containing one or more selected from among halogen, nitrogen, oxygen, silicon, a sulfur and phosphorus; (C1-C20)alkoxy;

(C6-C30)aryloxy; formyl; (C1-C20)alkylcarbonyl; (C6-C20)arylcarbonyl; a metalloid radical of Group 14 metal substituted with hydrocarbyl; a protonated group of the following Chemical Formula 2; a protonated group of the following Chemical Formula 3; a protonated group of the following Chemical Formula 4; a protonated group of the following Chemical Formula 5; a protonated group of the following Chemical Formula 6; a protonated group of the following Chemical Formula 7; a protonated group of the following Chemical Formula 8; or a protonated group of the following Chemical Formula 9;

wherein at least one or more of $R^1$ to $R^{10}$ are a protonated group selected from a group consisting of the following Chemical Formulas 2, 3, 4, 5, 6, 7, 8, and 9;

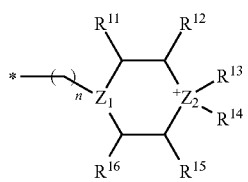

[Chemical Formula 2]

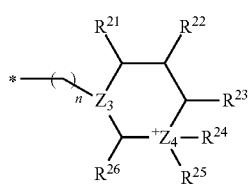

[Chemical Formula 3]

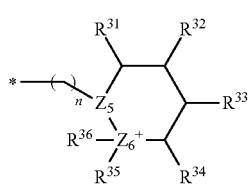

[Chemical Formula 4]

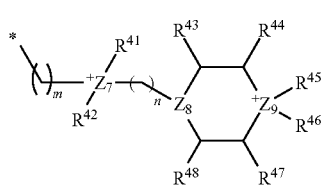

[Chemical Formula 5]

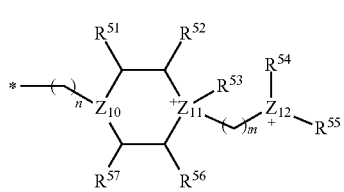

[Chemical Formula 6]

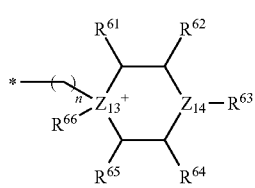

[Chemical Formula 7]

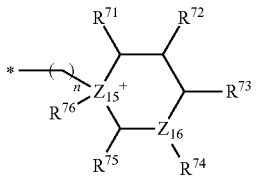

[Chemical Formula 8]

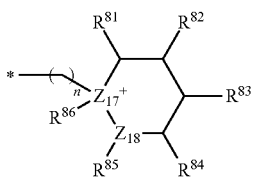

[Chemical Formula 9]

$X^-$ is halogen anion; a (C6-C20)aryloxy anion; a (C6-C20)aryloxy anion containing one or more selected from among halogen, nitrogen, oxygen, silicon, a sulfur and phosphorus; a (C1-C20)alkylcarboxy anion; a (C1-C20)alkylcarboxy anion containing one or more selected from among halogen, nitrogen, oxygen, silicon, a sulfur and phosphorus; a (C6-C20)arylcarboxy anion; a (C6-C20)arylcarboxy anion containing one or more selected from among halogen, nitrogen, oxygen, silicon, a sulfur and phosphorus; a (C1-C20)alkoxy anion; a (C1-C20)alkoxy anion containing one or more selected from among halogen, nitrogen, oxygen, silicon, a sulfur and phosphorus; a (C1-C20)alkylcarbonate anion; a (C1-C20)alkylcarbonate anion containing one or more selected from among halogen, nitrogen, oxygen, silicon, a sulfur and phosphorus; a (C6-C20)arylcarbonate anion; a (C6-C20)arylcarbonate anion containing one or more selected from among halogen, nitrogen, oxygen, silicon, a sulfur and phosphorus; a (C1-C20)alkylsulfonate anion; a (C1-C20)alkylsulfonate anion containing one or more selected from among halogen, nitrogen, oxygen, silicon, a sulfur and phosphorus; a (C1-C20)alkylamido anion; a (C1-C20)alkylamido anion containing one or more selected from among halogen, nitrogen, oxygen, silicon, a sulfur and phosphorus; a (C6-C20)arylamido anion; a (C6-C20)arylamido anion containing one or more selected from among halogen, nitrogen, oxygen, silicon, a sulfur and phosphorus; a (C1-C20)alkylcarbamate anion; a (C1-C20)alkylcarbamate anion containing one or more selected from among halogen, nitrogen, oxygen, silicon, a sulfur and phosphorus; a (C6-C20)arylcarbamate anion; or a (C6-C20)arylcarbamate anion containing one or more selected from among halogen, nitrogen, oxygen, silicon, a sulfur and phosphorus;

$X^-$ may be coordinated to M;

$Y_1^-$ is $F^-$, $Cl^-$, $Br^-$, $I^-$, $BF_4^-$, $ClO_4^-$, $NO_3^-$ or $PF_6^-$;

*$Y_2^{2-}$ is $SO_4^{2-}$ or $CO_3^{2-}$;

a is an integer obtained by adding 1 to the total number of monovalent cations included in protonated groups of $R^1$ to $R^{10}$;

b is an integer of 1 or more, c is an integer of 0 or more, d is an integer of 0 or more, and b+c+2d=a is satisfied;

$Z_1$ to $Z_{18}$ are each independently an nitrogen or phosphorus;

n is an integer of 1 to 10;

m is an integer of 1 to 10;

$R^{11}$ to $R^{16}$, $R^{21}$ to $R^{26}$, $R^{31}$ to $R^{36}$, $R^{41}$ to $R^{48}$, $R^{51}$ to $R^{57}$, $R^{61}$ to $R^{66}$, $R^{71}$ to $R^{76}$ and $R^{81}$ to $R^{86}$ are each independently hydrogen; (C1-C20)alkyl; (C1-C20)alkyl containing one or more selected from among halogen, nitrogen, oxygen, silicon, a sulfur and phosphorus; (C2-C20)alkenyl; (C2-C20)alkenyl containing one or more selected from among halogen, nitrogen, oxygen, silicon, a sulfur and phosphorus; (C1-C20)alkyl(C6-C20)aryl; (C1-C20)alkyl(C6-C20)aryl containing one or more selected from among halogen, nitrogen, oxygen, silicon, a sulfur and phosphorus; (C6-C20)aryl (C1-C20)alkyl; (C6-C20)aryl(C1-C20)alkyl containing one or more selected from among halogen, nitrogen, oxygen, silicon, a sulfur and phosphorus; or a metalloid radical of Group 14 metal substituted with hydrocarbyl; two of $R^{11}$ to $R^{16}$, two of $R^{21}$ to $R^{26}$, two of $R^{31}$ to $R^{36}$, two of $R^{41}$ to $R^{48}$, two of $R^{51}$ to $R^{57}$, two of $R^{61}$ to $R^{66}$, two of $R^{71}$ to $R^{76}$, and two of $R^{81}$ to $R^{86}$ may be linked with each other to thereby form a ring; and wherein alkyl, alkenyl, alkylaryl, arylalkyl, alkoxy, aryloxy, alkylcarbonyl, and arylcarbonyl of $R^1$ to $R^{10}$, and alkyl, alkenyl, alkylaryl and arylalkyl of $R^{11}$ to $R^{16}$, $R^{21}$ to $R^{26}$, $R^{31}$ to $R^{36}$, $R^{43}$ to $R^{48}$, $R^{51}$ to $R^{57}$, $R^{61}$ to $R^{66}$, $R^{71}$ to $R^{76}$ and $R^{81}$ to $R^{86}$ may be further substituted with any one or more selected from halogen, (C1-C20) alkyl, (C2-C20)alkenyl, (C1-C20)alkyl(C6-C20)aryl and (C6-C20)aryl(C1-C20)alkyl.

2. The complex of claim 1, wherein Q is (C6-C30)arylene, (C1-C20)alkylene, (C2-C20)alkenylene, (C2-C20)alkynylene or (C3-C20)cycloalkylene.

3. The complex of claim 2, wherein
M is trivalent cobalt;
A is oxygen; and
Q is 1,2-cyclohexylene, phenylene or ethylene.

4. The complex of claim 1, wherein at least one or more of $R^1$, $R^2$, $R^5$ and $R^6$ are a protonated group selected from a group consisting of Chemical Formulas 2, 3, 4, 5, 6, 7, 8, and 9 of claim 1.

5. The complex of claim 4, wherein $R^3$, $R^4$, $R^7$, $R^8$, $R^9$ and $R^{10}$ are hydrogen.

6. The complex of claim 5, which has a structure represented by the following Chemical Formula 11:

[Chemical Formula 11]

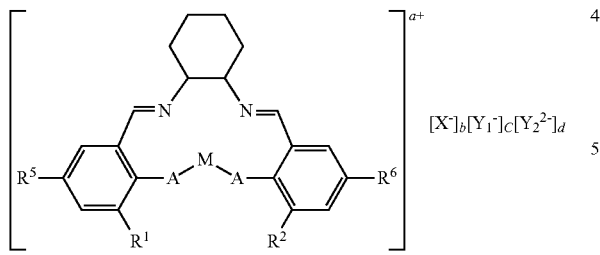

in Chemical Formula 11,
M is trivalent cobalt or trivalent chromium;
A is oxygen or sulfur;
$R^1$ and $R^2$ are each independently a protonated group selected from a group consisting of hydrogen, (C1-C10)alkyl, Chemical Formulas 2, 3, 4, 5, 6, 7, 8, and 9 of claim 1;
$R^5$ and $R^6$ identically represent hydrogen, halogen, (C1-C20)alkyl, (C2-C20)alkenyl, (C1-C20)alkoxy, (C1-C20)alkyl(C6-C20)aryl or (C6-C20)aryl(C1-C20) alkyl; alkyl, alkenyl, alkoxy, alkylaryl or arylalkyl of $R^5$ or $R^6$ may be further substituted with any one or more selected from halogen, (C1-C20)alkyl, (C2-C20) alkenyl, (C1-C20)alkoxy, (C1-C20)alkyl(C6-C20) aryl or (C6-C20)aryl(C1-C20)alkyl;

$X_1^-$ is halogen anion; a (C1-C20)alkylcarboxy anion; a (C1-C20)alkylcarboxy anion containing one or more selected from among halogen, nitrogen, oxygen, silicon, a sulfur and phosphorus; a (C1-C20)alkylcarbonate anion; a (C1-C20)alkylcarbonate anion containing one or more selected from among halogen, nitrogen, oxygen, silicon, a sulfur and phosphorus; a (C1-C20) alkylcarbamate anion; or a (C1-C20)alkylcarbamate anion containing one or more selected from among halogen, nitrogen, oxygen, silicon, a sulfur and phosphorus; a (C6-C20)aryloxy anion; or a (C6-C20)aryloxy anion containing one or more selected from among halogen, nitrogen, oxygen, silicon, a sulfur and phosphorus;

$X_1^-$ may be coordinated to Co;

$Y_1^-$ is $Cl^-$, $Br^-$, $BF_4^-$ or $NO_3^-$;

$Y_2^{2-}$ is $SO_4^{2-}$ or $CO_3^{2-}$;

a is an integer obtained by adding 1 to the total number of monovalent cations included in protonated groups of $R^1$ to $R^2$; and b is an integer of 1 or more, c is an integer of 0 or more, d is an integer of 0 or more, and b+c+2d=a is satisfied.

7. The complex of claim 6, which has a structure represented by any one of the following Chemical Formulas 12 to 22:

[Chemical Formula 12]

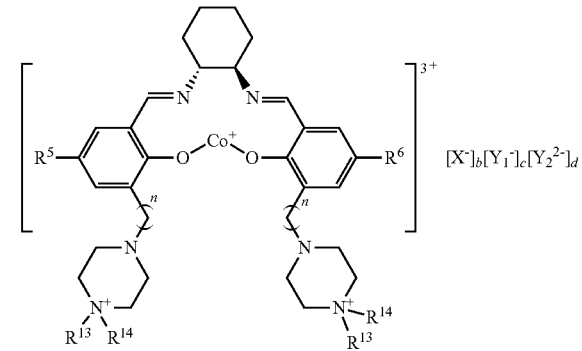

[Chemical Formula 13]

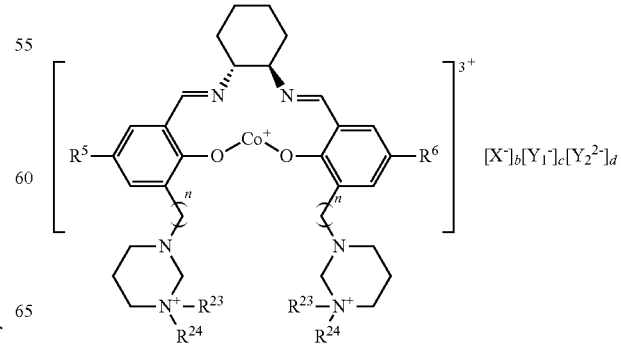

[Chemical Formula 14]
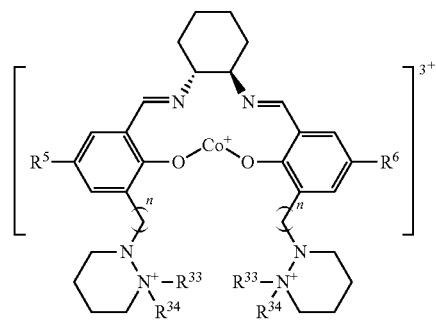
[X⁻]_b[Y₁⁻]_c[Y₂²⁻]_d
[Chemical Formula 15]
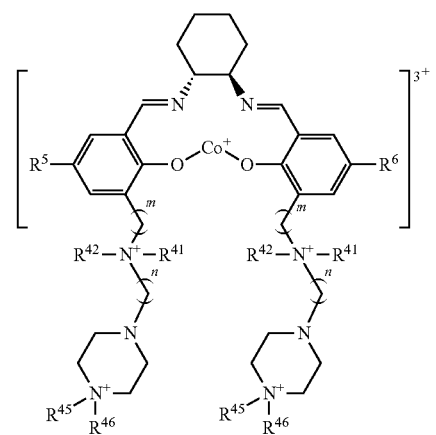
[X⁻]_b[Y₁⁻]_c[Y₂²⁻]_d
[Chemical Formula 16]
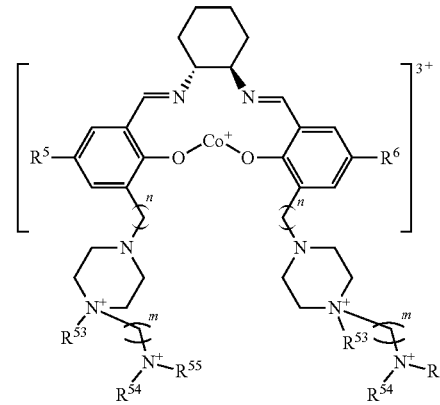
[X⁻]_b[Y₁⁻]_c[Y₂²⁻]_d
[Chemical Formula 17]
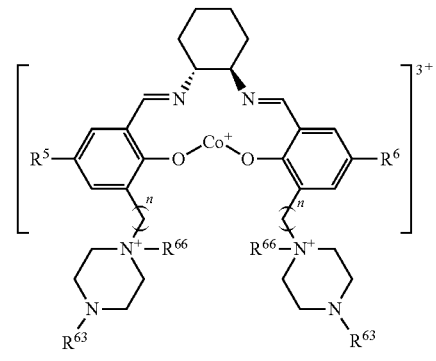
[X⁻]_b[Y₁⁻]_c[Y₂²⁻]_d
[Chemical Formula 18]
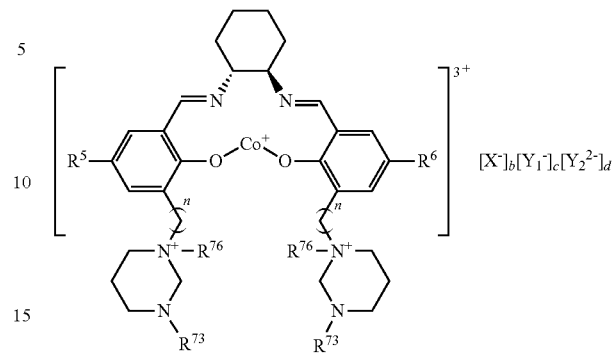
[X⁻]_b[Y₁⁻]_c[Y₂²⁻]_d
[Chemical Formula 19]
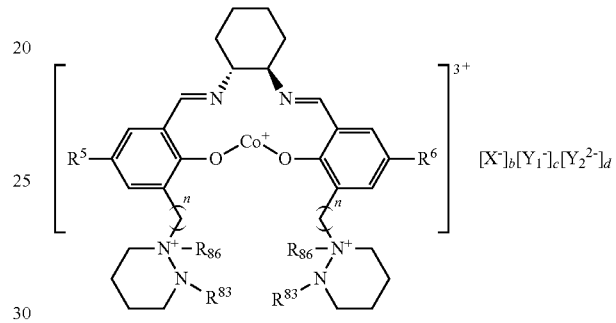
[X⁻]_b[Y₁⁻]_c[Y₂²⁻]_d
[Chemical Formula 20]
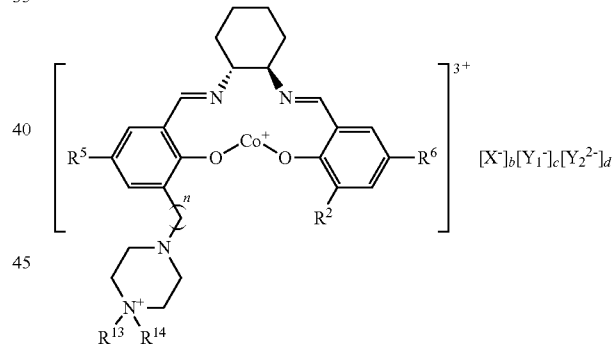
[X⁻]_b[Y₁⁻]_c[Y₂²⁻]_d
[Chemical Formula 21]
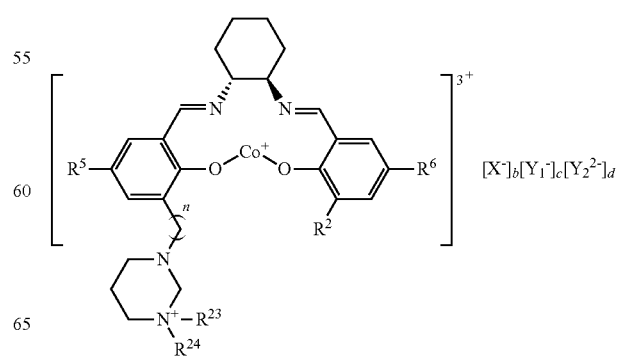
[X⁻]_b[Y₁⁻]_c[Y₂²⁻]_d

[Chemical Formula 22]

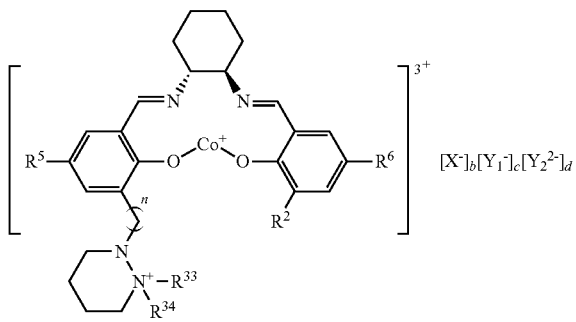

in Chemical Formulas 12 to 22,
$R^2$ is hydrogen or (C1-C20)alkyl;
$R^5$ or $R^6$ is hydrogen, halogen, (C1-C10)alkyl or (C1-C10)alkoxy;
$R^{13}$, $R^{14}$, $R^{23}$, $R^{24}$, $R^{33}$, $R^{34}$, $R^{41}$, $R^{42}$, $R^{45}$, $R^{46}$, $R^{53}$, $R^{54}$, $R^{55}$, $R^{63}$, $R^{66}$, $R^{73}$, $R^{76}$, $R^{83}$ and $R^{86}$ are each independently (C1-C10)alkyl;
m or n is each independently an integer of 1 to 10;
*$X^-$ is $Cl^-$, an acetate anion ($CH_3COO^-$) or a 4-nitrophenoxy anion ($NO_2$—$C_6H_5O^-$);
$X^-$ may be coordinated to Co;
$Y_1^-$ is $Cl^-$, $Br^-$ or $NO_3^-$;
$Y_2^{2-}$ is $SO_4^{2-}$ or $CO_3^{2-}$; and
b is an integer of 1 or more, c is an integer of 0 or more, d is an integer of 0 or more, and b+c+2d=3 is satisfied.

8. A preparation method of poly(alkylene carbonate), comprising: copolymerizing carbon dioxide and one or more epoxide compound selected from a group consisting of (C2-C20)alkylene oxide unsubstituted or substituted with halogen, (C1-C20)alkyloxy, (C6-C20)aryloxy or (C6-C20)ar(C1-C20)alkyl(aralkyl)oxy; (C4-C20)cycloalkylene oxide unsubstituted or substituted with halogen, (C1-C20)alkyloxy, (C6-C20)aryloxy or (C6-C20)ar(C1-C20)alkyl(aralkyl)oxy; and (C8-C20)styrene oxide unsubstituted or substituted with halogen, (C1-C20)alkyloxy, (C6-C20)aryloxy, (C6-C20)ar(C1-C20)alkyl(aralkyl)oxy or (C1-C20)alkyl in the presence of a compound represented by the following Chemical Formula 31 which is a molecular weight regulator, using the complex of claim 1 as a catalyst:

J(LH)$_c$   [Chemical Formula 31]

in Chemical Formula 31, J is C1 to C60 hydrocarbyl c-valent radical with or without an ether group, an ester group or an amine group; LH is —OH or —$CO_2H$; and c is an integer from 1 to 10, in which LH may be identical or different when c is 2 or more.

9. The preparation method of claim 8, wherein in the compound represented by Chemical Formula 31, c is 1; and J is C1 to C60 hydrocarbyl radical with or without an ether group, an ester group, or an amine group.

10. The preparation method of claim 8, wherein in the compound represented by Chemical Formula 31, c is 2; and J is C1 to C60 hydrocarbyl diradical with or without an ether group, an ester group, or an amine group.

11. The preparation method of claim 10, wherein in the compound represented by Chemical Formula 31, LH is —$CO_2H$; and J is —[$CR_2$]$_n$— (n is an integer of 0 to 20; and R which may be identical or different represents hydrogen, methyl, ethyl, propyl, or butyl), para-phenylene, meta-phenylene, ortho-phenylene or 2,6-naphthalenediyl.

12. The preparation method of claim 10, wherein in the compound represented by Chemical Formula 31, LH is —OH; and J is —[$CR_2$]$_n$— (n is an integer of 0 to 20; and R which may be identical or different represents hydrogen, methyl, ethyl, propyl, or butyl), —$CH_2CH_2N(R)CH_2CH_2$— (R is C1 to C20 hydrocarbyl) or [$CH_2CH(R)O$]$_n CH_2CH(R)$— (n is an integer of 0 to 10; and R is hydrogen or methyl).

13. The preparation method of claim 9, wherein in the compound represented by Chemical Formula 31, LH is —OH; and J is —[$CR_2$]$_n$— (n is an integer of 0 to 20; and R which may be identical or different represents hydrogen, methyl, ethyl, propyl, or butyl).

14. The preparation method of claim 8, wherein in the compound represented by Chemical Formula 31, c is 3; and J is C1 to C60 hydrocarbyl triradical with or without an ether group, an ester group, or an amine group.

15. The preparation method of claim 14, wherein in the compound represented by Chemical Formula 31, LH is —$CO_2H$; and J is 1,2,3-propanetriyl, 1,2,3-benzenetriyl, 1,2,4-benzenetriyl or 1,3,5-benzenetriyl.

16. The preparation method of claim 8, wherein in the compound represented by Chemical Formula 31, c is 4; and J is C1 to C60 hydrocarbyl tetraradical with or without an ether group, an ester group, or an amine group.

17. The preparation method of claim 16, wherein in the compound represented by Chemical Formula 31, LH is —$CO_2H$; and J is 1,2,3,4-butanetetrayl or 1,2,4,5-benzenetetrayl.

* * * * *